(12) United States Patent
Mori et al.

(10) Patent No.: US 9,238,757 B2
(45) Date of Patent: Jan. 19, 2016

(54) BONDING METHOD, BONDABILITY IMPROVING AGENT, SURFACE MODIFICATION METHOD, SURFACE MODIFYING AGENT, AND NOVEL COMPOUND

(75) Inventors: Kunio Mori, Morioka (JP); Yusuke Matsuno, Morioka (JP); Katsuhito Mori, Morioka (JP); Takahiro Kudo, Morioka (JP)

(73) Assignees: Kunio Mori, Morioka-shi (JP); Sulfur Chemical Laboratory Incorporated, Morioka-shi (JP)

( * ) Notice: Subject to any disclaimer, the term of this patent is extended or adjusted under 35 U.S.C. 154(b) by 344 days.

(21) Appl. No.: 13/823,759
(22) PCT Filed: Sep. 28, 2011
(86) PCT No.: PCT/JP2011/072185
§ 371 (c)(1),
(2), (4) Date: Mar. 15, 2013
(87) PCT Pub. No.: WO2012/043631
PCT Pub. Date: Apr. 5, 2012

(65) Prior Publication Data
US 2013/0177770 A1 Jul. 11, 2013

(30) Foreign Application Priority Data
Sep. 30, 2010 (JP) ................................. 2010-220512

(51) Int. Cl.
*C09J 5/00* (2006.01)
*C07F 7/18* (2006.01)
*C07F 5/06* (2006.01)

(52) U.S. Cl.
CPC . *C09J 5/00* (2013.01); *C07F 5/068* (2013.01); *C07F 7/1836* (2013.01); *C09J 2205/31* (2013.01); *C09J 2483/00* (2013.01); *Y10T 428/31536* (2015.04)

(58) Field of Classification Search
CPC ......................................................... C09J 5/00

USPC .............................. 428/420; 156/330.9, 272.2
See application file for complete search history.

(56) References Cited

U.S. PATENT DOCUMENTS

| 4,969,951 A | 11/1990 | Koike et al. |
| 6,011,135 A * | 1/2000 | Mori .................... C07D 251/46 528/373 |

(Continued)

FOREIGN PATENT DOCUMENTS

| CN | 1382195 A | 11/2002 |
| JP | 61 266468 | 11/1986 |

(Continued)

OTHER PUBLICATIONS

Mori, K., "The 21th Century Adhesion Technology," Journal of the Adhesion Society of Japan, vol. 43, No. 6, pp. 242-248, (2007) (with English translation).

(Continued)

*Primary Examiner* — Daniel Lee
(74) *Attorney, Agent, or Firm* — Oblon, McClelland, Maier & Neustadt, L.L.P.

(57) ABSTRACT

To provide a technique by which an —OH group can be effectively formed on a material surface for the purpose of making the material suitable for bonding (for example, for molecular bonding) that utilizes a chemical reaction (chemical binding). [Solution] A bonding method for bonding a substrate A and a substrate B, which comprises: a step for applying an agent that contains the compound (α) described below on the surface of the substrate A; a step for arranging the substrate B so as to face the compound (α) that is present on the surface of the substrate A; and a step for integrally bonding the substrate A and the substrate B by applying a force onto the substrate A and/or the substrate B. The compound (α) is a compound that has an OH group or an OH-forming group, an azide group and a triazine ring in each molecule, and the substrate A is configured using a polymer.

22 Claims, 1 Drawing Sheet

(56) References Cited

U.S. PATENT DOCUMENTS

2008/0311412 A1    12/2008   Fokin et al.
2010/0080893 A1    4/2010   Inoue et al.
2011/0104505 A1    5/2011   Mori et al.

FOREIGN PATENT DOCUMENTS

| JP | 2006 213677 | 8/2006 |
|---|---|---|
| JP | 2007 17921 | 1/2007 |
| JP | 2007 119752 | 5/2007 |
| JP | 2008 507404 | 3/2008 |
| JP | 3168511 | 6/2011 |
| WO | WO 2009/154083 A1 | 12/2009 |

OTHER PUBLICATIONS

Mori, K., et al., "Sixivalent Chromate-Free Resin Plating—A Molecular Adhesion Method-,"Journal of the Surface Finishing Society of Japan, vol. 59, No. 5, pp. 299-304, (2008) (with English translation).

Takagi, K., et al., "Direct Adhesion of Silicone Rubber to Resins During Peroxide Curing Using Molecular Adhesive," The Society of Rubber Industry, Japan, vol. 81, pp. 8-13, (2008) (with English abstract).

Mori, K., et al., "Direct Adhesion of Epichlorohydrin Rubber to Polyamide 6 During Curing Using a Molecular Adhesive," The Society of Rubber Industry, Japan, vol. 83, No. 3, pp. 71-76, (2010) (with English abstract).

Matsuno, Y., et al., "Direct Adhesion of EPDM to Aluminum Plate During Peroxide Curing Using Molecular Adhesives," The Society of Rubber Industry, Japan, vol. 83, No. 4, pp. 89-94, (2010) (with English abstract).

"June Regular Meeting of Plating Section-Lecture and Field Trip-," The Surface Finishing Society of Japan, Plating Section, pp. 1-8 (Jun. 5-6, 2008) (with English translation).

International Search Report Issued Nov. 1, 2011 in PCT/JP11/72185 Filed Sep. 28, 2011.

U.S. Appl. No. 13/823,526, filed Apr. 4, 2013, Mori, et al.

Combined Chinese Office Action and Search Report issued Oct. 11, 2013 in Patent Application No. 201180041291.3 (with English language translation).

"STN Columbus" STN Search Report, Sep. 26, 2013, 10 Pages.

Takahiro Kakuda "Photosensitive Resin" Science Publishing Company, Feb. 1978, 4 pages (with partial English language translation).

Chinese Search Report issued May 6, 2014 in Patent Application No. 201180041291.3 with Partial English Translation.

Taiwanese Search Report issued Nov. 20, 2013 in Patent Application No. 100135711 with English Translation of Category of Cited Documents.

Philippe Roger et al., "Surface Characterizations of Poly(ethylene terephthalate) Film Modified by a Carbohydrate-bearing Photoreactive Azide Group", European Polymer Journal, vol. 46, Apr. 9, 2010, pp. 1594-1603.

\* cited by examiner

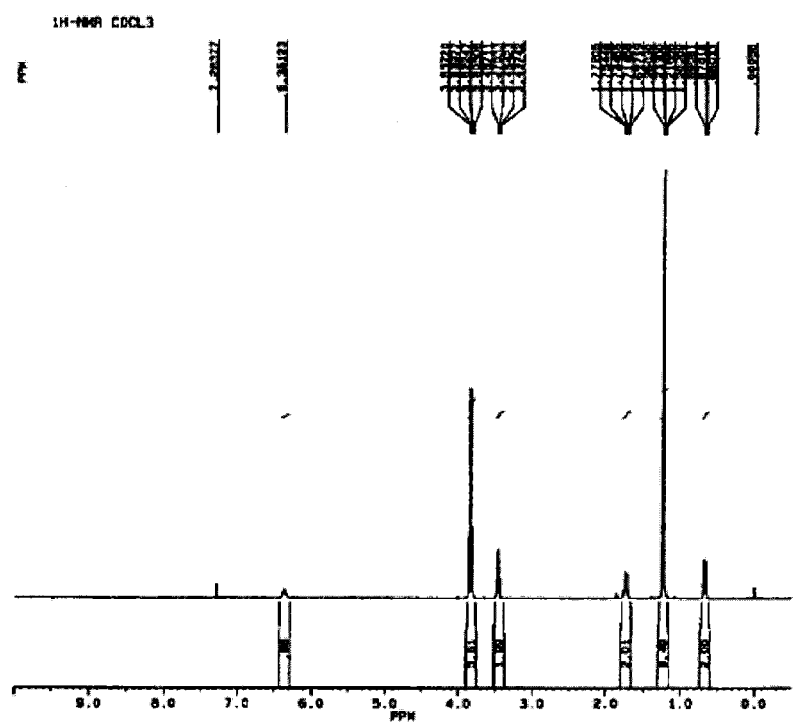
FIG. 2
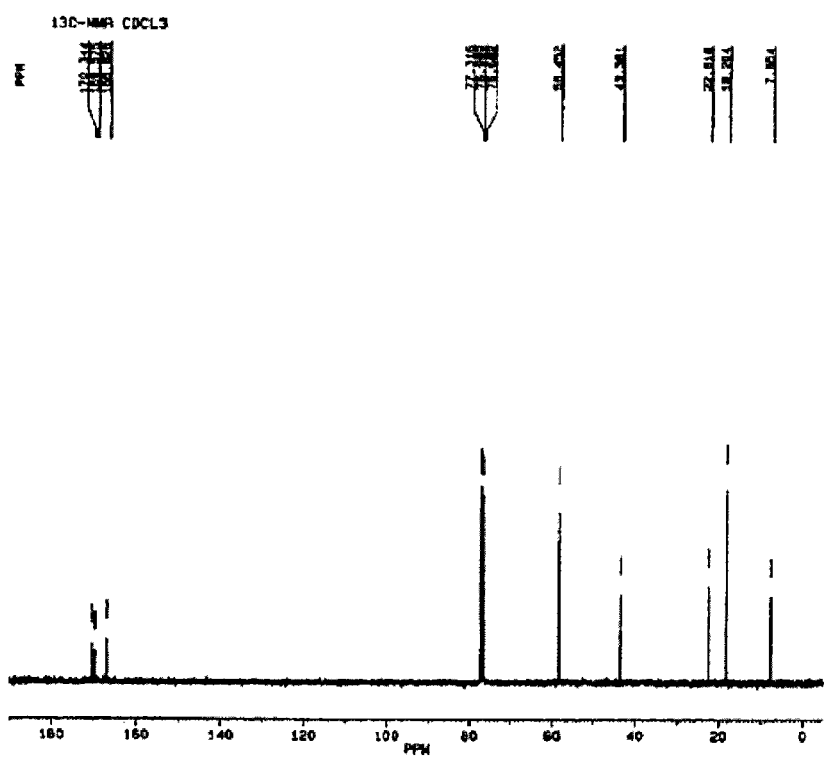

BONDING METHOD, BONDABILITY IMPROVING AGENT, SURFACE MODIFICATION METHOD, SURFACE MODIFYING AGENT, AND NOVEL COMPOUND

TECHNICAL FIELD

The present invention relates to a bonding method, an adhesiveness improving agent, a surface modification method, a surface modifying agent, and a novel compound.

BACKGROUND ART

As technologies for bonding a material A and a material B, there exist:

(1) A bonding technology using mechanical means (for example, bolts and nuts, or rivets), (2) A bonding technology using welding means (for example, solders or brazing filler metals), and (3) A bonding technology using adhesives The aforementioned bonding technology (3) is employed in a wide-range fields. However, with regard to the adhesives to be employed for boding (adhesion) between the material A and the material B, it cannot be safely said that any type of the adhesives may be used. It is of importance to select the adhesives suitable for the material A and the material B. The adhesion conditions are also of importance. This means that employment of the conventional bonding technology (3) is not a simple matter. That is, the bonding technology employing the adhesives used so far is unsatisfactory.

A basis (basic point) of the adhesion by the conventional adhesives is founded on a phenomenon "wetting". The aforementioned "wetting" phenomenon is governed by a kind of materials, a surface status (properties) of materials, an environment in the neighborhood, and the like. This has commonality with the fact that selection of the adhesives and selection of the adhesion conditions are of importance.

"Wetting" obeys to a law of free energy to be derived from a law of thermodynamics. Wetting of fluid for non-fluid is expressed by an interaction constant $\chi$ of both. $\chi$ existing in a scope of the wetting is 0 to 0.5. $\chi$ is comprised of an entropy term and an enthalpy term. In a high polymerized material (polymer), the aforementioned entropy term is approximately 0.34 in an experimental manner. The aforementioned $\chi$ is 0 to 0.45 when the wetting property is excellent. Thus, the remaining enthalpy term is at most 0.11 when the wetting property is excellent. The utilizable adhesion wetting is only 22% in terms of contribution when the interaction constant $\chi$ between the fluid and the non-fluid is 0.5. In such a manner, upon mentioning the wetting, a ratio of the wetting contributing to the adhesion is 22% of the entire wetting or less. This means that it is possible to manipulate adhesion factors only in very narrow scope. That is, the adhesion by the conventional adhesives is adhesion that is high in material dependency. And, the adhesion technology having a philosophy that an original point of the adhesion is "wetting" is high in material dependency. And yet, the intentional adhesion is difficult. In addition, reliability of the adhesion as well becomes a subject of discussion because an adhesive strength depends on the wetting (namely, intermolecular force). For example, the aforementioned wetting (namely, intermolecular force: adhesive strength) also fluctuates when the environment in which an adhesive interface exists is changed due to the adhesives. This causes a reliability of the adhesion to decline.

The adhesives (which is sometimes referred to as "molecular adhesives" in this specification) applying the chemical bonding (chemical reaction) has been proposed by this inventor instead of the adhesives applying the conventional wetting (intermolecular force: physical force) (Patent literatures 1, 2, and 3, and non-patent literatures 1, 2, 3, 4, and 5).

CITATION LIST

Patent Literature

PTL 1: JP-P2006-213677A
PTL 2: JP-P2007-17921A
PTL 3: JP-P2007-119752A

Non-Patent Literature

NON-PTL 1: MORI Kunio "The 21th Century Adhesion Technology", Journal of the Adhesion Society of Japan, vol. 43(6), 242-248 (2007)
NON-PTL 2: MORI Kunio and ABE Shiro "Sixvalent Chromate-Free Resin Plating, Journal of the Surface Finishing Society of Japan, vol. 59(5), 299-304 (2008)
NON-PTL 3: TAKAGI Kazuhisa, HIRAHARA Hidetoshi, MORI Katsuhito, NARITA Eiichi, OISHI Yoshiyuki, and MORI Kunio "Direct Adhesion of Silicone Rubber to Resins During Peroxide Curing Using Molecular Adhesive", The Society of Rubber Industry, Japan 81, 8-13 (2008)
NON-PTL 4: MORI Katsuhito, MATSUNO Yusuke, MURAOKA Hiroki, KUDO Takahiro, HIRAHARA Hidetoshi, OISHI Yoshiyuki, MORI Kunio, and NARITA Eiichi "Direct Adhesion of Epichlorohydrin Rubber to Polyamide 6 During Curing Using a Molecular Adhesive", The Society of Rubber Industry, Japan 83(3) 71-76 (2010)
NON-PTL 5: MATSUNO Yusuke, KUDO Takahiro, NIWA Ako, HIRAHARA Hidetoshi, NARITA Eiichi, OISHI Yoshiyuki, and MORI Kunio "Direct Adhesion of EPDM to Aluminum Plate During Peroxide Curing Using Molecular Adhesives", The Society of Rubber Industry, Japan 83(4) 89-94 (2010)

SUMMARY OF INVENTION

Technical Problem

In the above-mentioned technologies, for example, a corona discharge treatment (pretreatment) is performed. With this corona discharge treatment, —OH is generated on the material surface. The chemical reaction occurs between this —OH generated on the material surface and the molecular adhesive, and the molecular adhesives is strongly bonded to the material (adhesion: bonding).

However, there were many cases in which —OH was not sufficiently generated even though the corona discharge treatment was performed.

Besides, with the case in which the material is a high polymerized material (polymer), the material might be deteriorated (decomposed) when the corona discharge treatment is performed. The adhesive strength declines when this decomposed product is left on the material surface. This necessitates cleaning after the corona discharge treatment. However, —OH generated on the surface decreases when the cleaning is performed with a solvent. Thus, in this case, the meaning of the corona discharge treatment lowers.

And yet, the corona discharge treatment incurs a constraint to size and shape of the material, being a target of adhesion. Moreover, the corona discharge is no good in workability.

Thus, the present invention has been accomplished in consideration of the above-mentioned problems, and a task thereof is to provide the technology that enables —OH to be effectively introduced into the material surface even though the corona discharge treatment is not performed. In particular, a task thereof is to provide the technology that enables —OH to be effectively introduced into the material surface, so as to make the adhesion (for example, the molecular adhesion) utilizing the chemical reaction (chemical bonding) preferred.

Means for Solving Problem

The aforementioned problem is solved by a bonding method of bonding a base A and a base B, which is characterized in including a step (X) of applying an agent containing the following compound (α) onto a surface of the aforementioned base A, and a step (Y) of arranging the aforementioned base B so as to face the aforementioned compound (α) existing on the aforementioned base A surface, and a step (Z) of applying force onto the aforementioned base A and/or the aforementioned base B to integrally bond the aforementioned base A and the aforementioned base B, wherein the aforementioned compound (α) is a compound having at least one OH group or at least one OH yielding group, at least one azide group, and at least one triazine ring per molecule, and the aforementioned base A is configured by employing a polymer.

Preferably, the aforementioned problem is solved by the aforementioned bonding method, which is characterized in that the force to be applied in the aforementioned step (Z) is force such that OH groups of the aforementioned compound (α) existing on the aforementioned base A surface, or OH groups generated from OH yielding groups thereof come into contact with the surface of the aforementioned base B due to the aforementioned force.

Preferably, the aforementioned problem is solved by the aforementioned bonding method, which is characterized in that the aforementioned step (Z) is performed at a temperature of 0 to 300° C.

Preferably, the aforementioned problem is solved by the aforementioned bonding method, which is characterized in further including a step (W) of irradiating the aforementioned compound (α) existing on the surface of the aforementioned base A with light having a predetermined pattern.

Preferably, the aforementioned problem is solved by the aforementioned bonding method, which is characterized in that light irradiation of the aforementioned step (W) allows the aforementioned base A and the azide group of the aforementioned compound (α) to chemically react to each other, and the aforementioned compound (α) to be bonded to the surface of the aforementioned base A.

Preferably, the aforementioned problem is solved by the aforementioned bonding method, which is characterized in that the aforementioned light is ultraviolet rays.

Preferably, the aforementioned problem is solved by the aforementioned bonding method, which is characterized in that the aforementioned OH group or OH yielding group is an alkoxysilyl group (the case in which an alkoxy group in the aforementioned alkoxysilyl group is the OH group is also included).

Preferably, the aforementioned problem is solved by the aforementioned bonding method, which is characterized in that the aforementioned compound (α) is a compound represented by the following general formula [I].

Preferably, the aforementioned problem is solved by the aforementioned bonding method, which is characterized in that the aforementioned compound (α) is a compound represented by the following general formula [Io].

Preferably, the aforementioned problem is solved by the aforementioned bonding method, which is characterized in that the aforementioned compound (α) is a compound represented by the following general formula [Ia].

Preferably, the aforementioned problem is solved by the aforementioned bonding method, which is characterized in that the aforementioned compound (α) is a compound represented by the following general formula [Ib].

Preferably, the aforementioned problem is solved by the aforementioned bonding method, which is characterized in further including a step (V) of applying a substance represented by the following general formula [II] onto the surface of the aforementioned compound (α) after the aforementioned step (X) and yet before the aforementioned step (Y).

Preferably, the aforementioned problem is solved by the aforementioned bonding method, which is characterized in further including a step (U) of applying a compound (β) having an alkoxysilyl group, an alkoxy aluminate group, and/or an alkoxy titanate group onto the surface of the aforementioned compound (α) after the aforementioned step (X) or step (V) and yet before the aforementioned step (Y). Preferably, the aforementioned compound (β) is a compound represented by the following general formula [T], general formula [III], or general formula [IV], The aforementioned problem is solved by a bonded body, which is characterized in being produced by integrally bonding the aforementioned base A and the aforementioned base B with the aforementioned bonding method.

The aforementioned problem is solved by an adhesiveness improver, which is characterized in including a compound (α) having at least one OH group or at least one OH yielding group, at least one azide group, and at least one triazine ring per molecule.

Preferably, the aforementioned problem is solved by the aforementioned adhesiveness improver, which is characterized in being an adhesive improver applied onto the surface of the base A configured by employing a polymer.

Preferably, the aforementioned problem is solved by the aforementioned adhesiveness improver, which is characterized in that the aforementioned OH group or OH yielding group is an alkoxysilyl group (the case in which an alkoxy group in the aforementioned alkoxysilyl group is the OH group is also included).

Preferably, the aforementioned problem is solved by the aforementioned adhesiveness improver, which is characterized in that the aforementioned compound (α) is a compound represented by the following general formula [I].

Preferably, the aforementioned problem is solved by the aforementioned adhesiveness improver, which is characterized in that the aforementioned compound (α) is a compound represented by the following general formula [Io].

Preferably, the aforementioned problem is solved by the aforementioned adhesiveness improver, which is characterized in that the aforementioned compound (α) is a compound represented by the following general formula [Ia].

Preferably, the aforementioned problem is solved by the aforementioned adhesiveness improver, which is characterized in that the aforementioned compound (α) is a compound represented by the following general formula [Ib].

The aforementioned problem is solved by a surface modification method of modifying properties of a base surface, which is characterized in including a step of applying a surface modifying agent onto the surface of the base, wherein the aforementioned surface modifying agent includes a compound (α) having at least one OH group or at least one OH yielding group, at least one azide group, and at least one triazine ring per molecule.

Preferably, the aforementioned problem is solved by the aforementioned surface modification method, which is characterized in further including a step of radiating light after the aforementioned surface modifying agent is applied.

Preferably, the aforementioned problem is solved by the aforementioned surface modification method, which is characterized in that the aforementioned light irradiation step is a step of performing photographic exposure in a predetermined pattern.

Preferably, the aforementioned problem is solved by the aforementioned surface modification method, which is characterized in that the aforementioned OH group or OH yielding group is an alkoxysilyl group (the case in which an alkoxy group in the aforementioned alkoxysilyl group is the OH group is also included).

Preferably, the aforementioned problem is solved by the aforementioned surface modification method, which is characterized in that the aforementioned compound (α) is a compound represented by the following general formula [I].

Preferably, the aforementioned problem is solved by the aforementioned surface modification method, which is characterized in that the aforementioned compound (α) is a compound represented by the following general formula [Io].

Preferably, the aforementioned problem is solved by the aforementioned surface modification method, which is characterized in that the aforementioned compound (α) is a compound represented by the following general formula [Ia].

Preferably, the aforementioned problem is solved by the aforementioned surface modification method, which is characterized in that the aforementioned compound (α) is a compound represented by the following general formula [Ib].

The aforementioned problem is solved by a surface modifying agent, which is characterized in including a compound (α) having at least one OH group or at least one OH yielding group, at least one azide group, and at least one triazine ring per molecule.

Preferably, the aforementioned problem is solved by the aforementioned surface modifying agent, which is characterized in that the aforementioned OH group or OH yielding group is an alkoxysilyl group (the case in which an alkoxy group in the aforementioned alkoxysilyl group is the OH group is also included).

Preferably, the aforementioned problem is solved by the aforementioned surface modifying agent, which is characterized in that the aforementioned compound (α) is a compound represented by the following general formula [I].

Preferably, the aforementioned problem is solved by the aforementioned surface modifying agent, which is characterized in that the aforementioned compound (α) is a compound represented by the following general formula [Io].

Preferably, the aforementioned problem is solved by the aforementioned surface modifying agent, which is characterized in that the aforementioned compound (α) is a compound represented by the following general formula [Ia].

Preferably, the aforementioned problem is solved by the aforementioned surface modifying agent, which is characterized in that the aforementioned compound (α) is a compound represented by the following general formula [Ib].

The aforementioned problem is solved by a novel compound, which is characterized in being a compound represented by the following general formula [Io].

The aforementioned problem is solved by a novel compound, which is characterized in being a compound represented by the following general formula [Ia].

The aforementioned problem is solved by a novel compound, which is characterized in being a compound represented by the following general formula [Ib].

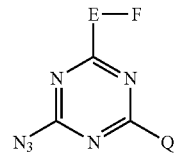

General formula [I]

[In the formula, E is an arbitrary group. F is an OH group or an OH yielding group. -Q is —$N_3$ or —$NR_1(R_2)$. Each of $R_1$ and $R_2$ of —$NR_1(R_2)$ is H, a hydrocarbon group having a carbon number of 1 to 24, or —$RSi(R')_n(OA)_{3-n}$ (R is a chain hydrocarbon group having a carbon number of 1 to 12. R' is a chain hydrocarbon group having a carbon number of 1 to 4. A is H or a chain hydrocarbon group having a carbon number of 1 to 4. n is an integer of 0 to 2). Each of $R_1$ and $R_2$ could be identical or could be different.]

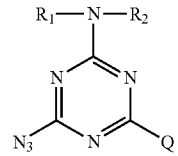

General formula [Io]

[In the formula, -Q is —$N_3$ or —$NR_1(R_2)$. Each of $R_1$ and $R_2$ is H, a hydrocarbon group having a carbon number of 1 to 24, or —$RSi(R')_n(OA)_{3-n}$ (R is a chain hydrocarbon group having a carbon number of 1 to 12. R' is a chain hydrocarbon group having a carbon number of 1 to 4. A is H or a chain hydrocarbon group having a carbon number of 1 to 4. n is an integer of 0 to 2). At least one, out of $R_1$ and $R_2$, is the aforementioned —$RSi(R')_n(OA)_{3-n}$. Each of $R_1$ and $R_2$ could be identical or could be different.]

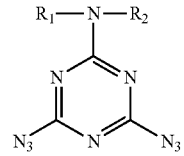

General formula [Ia]

[In the formula, each of $R_1$ and $R_2$ is H, a hydrocarbon group having a carbon number of 1 to 24, or —$RSi(R')_n(OA)_{3-n}$ (R is a chain hydrocarbon group having a carbon number of 1 to 12. R' is a chain hydrocarbon group having a carbon number of 1 to 4. A is H or a chain hydrocarbon group having a carbon number of 1 to 4. n is an integer of 0 to 2). At least one, out of $R_1$ and $R_2$, is the aforementioned —$RSi(R')_n(OA)_{3-n}$. Each of $R_1$ and $R_2$ could be identical or could be different.]

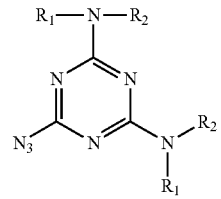

General formula [Ib]

[In the formula, each of $R_1$ and $R_2$ is H, a hydrocarbon group having a carbon number of 1 to 24, or —$RSi(R')_n$ $(OA)_{3-n}$ (R is a chain hydrocarbon group having a carbon number of 1 to 12. R' is a chain hydrocarbon group having a carbon number of 1 to 4. A is H or a chain hydrocarbon group having a carbon number of 1 to 4. n is an integer of 0 to 2). At least one, out of all $R_1$s and all $R_2$s, is the aforementioned —$RSi(R')_n(OA)_{3-n}$. Each of $R_1$ and $R_2$ could be identical or could be different.]

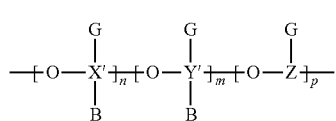

General formula [II]

[In the formula, each of X' and Y' is Si or Ti. Z is Al. G is a hydrocarbon group having a carbon number of 1 to 3 or an alkoxy group having a carbon number of 1 to 3. B is an alkoxy group having a carbon number of 1 to 3. Each of n and m is an integer of 0 to 200 (where 2≤n+m≤400). p is an integer of 0 to 100].

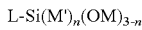

General formula [T]

[In the formula, L is an organic group (The organic group may contain elements other than carbon and hydrogen. The organic group may contain a substituent group. The organic group may assume any form of an aliphatic type, an aromatic type, a chain type and a cyclic type). M' is a chain hydrocarbon group having a carbon number of 1 to 4. M is H or a chain hydrocarbon group having a carbon number of 1 to 4. n is an integer of 0 to 2. Each of the aforementioned M' and M could be identical or could be different.]

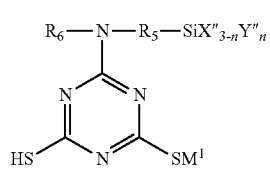

General formula [III]

[In the formula, $R_5$ is a hydrocarbon group having a carbon number of 1 to 12. $R_6$ is H or a hydrocarbon group having a carbon number of 1 to 10. X" is H or a hydrocarbon group having a carbon number of 1 to 10. Y" is an alkyloxy group having a carbon number of 1 to 10. n is an integer of 1 to 3. $M^1$ is H, Li, Na, K, or Cs.]

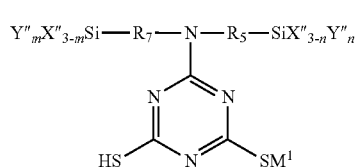

General formula [IV]

[In the formula, $R_5$ is a hydrocarbon group having a carbon number of 1 to 12. $R_7$ is a hydrocarbon group having a carbon number of 1 to 12. X" is H or a hydrocarbon group having a carbon number of 1 to 10. Y" is an alkyloxy group having a carbon number of 1 to 10. Each of all X"s and all Y"s could be identical to the other or could be different from the other. Each of n and m is an integer of 1 to 3. $M^1$ is H, Li, Na, K, or Cs.]

Advantageous Effect of Invention

—OH is effectively introduced into the surface of the high polymerized material even though the corona discharge treatment and the plasma discharge treatment are not performed.

The adhesion (for example, molecular adhesion) utilizing the chemical reaction (chemical bonding) is effectively performed. For this reason, the adhesive strength is strong. Moreover, endurance of the adhesion is high. For example, a fluctuation in the adhesive strength due to a change in the environment is small.

BRIEF DESCRIPTION OF DRAWINGS

FIG. 1 is a spectrum diagram of $^1$H-NMR of TE-DAZ.
FIG. 2 is a spectrum diagram of $^{13}$C-NMR of TE-DAZ.

DESCRIPTION OF EMBODIMENTS

A first present invention is a bonding method. In particular, the first present invention is a bonding method of bonding the base A and the base B. This bonding method includes a step (X), a step (Y), and a step (Z). The aforementioned step (X) is a step of applying the agent containing a compound (α) onto the surface of the aforementioned base A. The aforementioned step (Y) is a step of arranging the aforementioned base B so as to face the aforementioned compound (α) existing on the aforementioned base A surface. The aforementioned step (Z) is a step of applying force (press force (pressurization) or tensile force (decompression)) onto the aforementioned base A and/or the aforementioned base B to integrally bond the aforementioned base A and the aforementioned base B. The aforementioned compound (α) has at least one OH group or at least one OH yielding group, at least one azide group, and at least one triazine ring per molecule. The aforementioned base A is configured by employing a polymer.

The aforementioned step (X) is accomplished by immersing the base A into a solution containing the aforementioned compound (α) (for example, dissolved or dispersed). The aforementioned step (X) is also accomplished by blowing away the aforementioned solution onto the base A. Thereafter, the drying is performed according to a necessity. That is, the solvent is vaporized, thereby allowing the aforementioned compound (α) to be left on the base A surface. The aforementioned step (Y) is accomplished by piling up the aforementioned base A and the aforementioned base B. The aforementioned step (Z) is accomplished by exerting the press force facing the aforementioned base B side upon the aforementioned base A after the aforementioned step (Y). Or, the aforementioned step (Z) is accomplished by exerting the press force facing the aforementioned base A side upon the aforementioned base B. Needless to say, the press force facing the aforementioned base B side may be exerted upon the aforementioned base A and yet, the press force facing the aforementioned base A side may be exerted upon the aforementioned base B. Or, the aforementioned step (Z) is also accomplished by exerting the tensile force so that the aforementioned base A and the aforementioned base B come near.

Particularly preferably, the force applied in the aforementioned step (Z) is press force (tensile force) such that OH groups of the aforementioned compound (α) existing on the aforementioned base A surface, or OH groups generated from OH yielding groups thereof come into contact with the surface of the aforementioned base B due to the aforementioned force. With the case of the press force (pressurization), preferably, this force is 0.01 to 50 MPa (more preferably, 0.1 to 5 MPa). With the case of the tensile force (decompression), preferably, this force is 0.0099 to 0.00001 Pa (more preferably, 0.009 to 0.0001 Pa). The operating time of the force is, for example, 0.1 to 200 min. Needless to say, the operating time of the force is not limited hereto. The pressure and the time are appropriately selected. This allows the base A to be deformed accordingly even though minute irregularities exist on the surface of the base B. As a result, OH groups of the aforementioned compound (α) existing on the base A surface reach the surface of the aforementioned base B. And, OH groups are bonded to the surface of the aforementioned base B. That is, with the chemical bonding (reaction) by the aforementioned compound (α), the aforementioned base A and the aforementioned base B are strongly bonded to each other. The aforementioned step (Z) is preferably performed at a temperature of 0 to 300° C. More preferably, the aforementioned step (Z) is performed at a temperature of 20 to 250° C. With this, the chemical reaction between the OH groups of the aforementioned compound (α) and the aforementioned base B efficiently progresses.

Preferably, the aforementioned bonding method further includes a light irradiating step. That is, light is radiated toward the aforementioned compound (α) existing on the surface of the aforementioned base A. As a result, the aforementioned base A and the azide group of the aforementioned compound (α) chemically react to each other. And the aforementioned compound (α) is bonded to the surface of the aforementioned base A. The chemical reaction is not promoted in the location not irradiated with light. Thus, thereafter, when the washing is performed, a phenomenon that the aforementioned compound (α) exists on (has been bonded to) the surface of the aforementioned base A occurs only on the locations irradiated with light. It is enough to arrange masks in specific locations at the time of the light irradiation (light exposure) so as not to irradiate the specific locations with light. A reflective plate and a reflective film can be employed at the time of the light irradiation. This enhances irradiation efficiency. An irradiation scope spreads. The aforementioned light is preferably ultraviolet rays. Additionally, the heating means may be adopted instead of the light radiation. However, upon comparing the heating means and the light radiation means that was adopted in order to cause the aforementioned compound (α) to come into an excited state, the light radiation means was more desirable.

The OH group or OH yielding group of the aforementioned compound (α) is preferably an alkoxysilyl group (the case in which the aforementioned alkoxy group is the OH group is also included). In this case, the aforementioned compound (α) has at least one alkoxysilyl group and at least one azide group.

The aforementioned compound (α) has a structure in which at least one azide group and at least one alkoxysilyl group are preferably bonded to triazine directly or indirectly (among them, 1,3,5-triazine).

The aforementioned compound (α) is preferably a compound represented by the aforementioned general formula [I]. More preferably, the aforementioned compound (α) is a compound represented by the aforementioned general formula [Io]. Yet more preferably, the aforementioned compound (α) is a compound represented by the aforementioned general formulas [Ia] or [Ib].

In the aforementioned general formula, -Q is $—N_3$ or $—NR_1(R_2)$. Each of $R_1$ and $R_2$ is H, a hydrocarbon group having a carbon number of 1 to 24, or $—RSi(R')_n(OA)_{3-n}$ (R is a chain hydrocarbon group having a carbon number of 1 to 12. R' is a chain hydrocarbon group having a carbon number of 1 to 4. A is H or a chain hydrocarbon group having a carbon number of 1 to 4. n is an integer of 0 to 2). At least one, out of all $R_1$s and all $R_2$s, is the aforementioned $—RSi(R')_n(OA)_{3-n}$. Each of $R_1$ and $R_2$ could be identical or could be different.

In the aforementioned general formula [Ia], each of $R_1$ and $R_2$ is H, a hydrocarbon group having a carbon number of 1 to 24, or $—RSi(R')_n(OA)_{3-n}$. The aforementioned hydrocarbon group having a carbon number of 1 to 24 is a chain hydrocarbon group, a chain hydrocarbon group having a substituent group (cyclic or chain), a cyclic group, or a cyclic group having a substituent group (cyclic or chain). For example, each of $R_1$ and $R_2$ is $—C_nH_{2n+1}$, $—C_nH_{2n-1}$, $—C_6H_5$, $—CH_2CH_2C_6H_5$, $—CH_2C_6H_5$, $—C_{10}H_7$, or the like. R of the aforementioned $—RSi(R')_n(OA)_{3-n}$ is a chain hydrocarbon group having a carbon number of 1 to 12 (for example, $—C_nH_{2n}$). The aforementioned R' is a chain hydrocarbon group having a carbon number of 1 to 4 (for example, $—C_nH_{2n+1}$). The aforementioned A is H or a chain hydrocarbon group having a carbon number of 1 to 4 (for example, $—CH_3$, $—C_2H_5$, $—CH(CH_3)_2$, $—CH_2CH(CH_3)_2$, and $—C(CH_3)_3$). n is an integer of 0 to 2. At least one, out of $R_1$ and $R_2$, is the aforementioned $—RSi(R')_n(OA)_{3-n}$. Each of $R_1$ and $R_2$ could be identical or could be different. The so-called group having a substituent group (for example, hydrocarbon group) in this specification signifies a group in which for example, H of the aforementioned group (for example, hydrocarbon group) has been replaced with a substitutable appropriate functional group.

In the aforementioned general formula [Ib], each of $R_1$ and $R_2$ is H, a hydrocarbon group having a carbon number of 1 to 24, or $—RSi(R')_n(OA)_{3-n}$. The aforementioned hydrocarbon group having a carbon number of 1 to 24 is a chain hydrocarbon group, a chain hydrocarbon group having a substituent group (cyclic or chain), a cyclic group, or a cyclic group having a substituent group (cyclic or chain). For example, each of $R_1$ and $R_2$ is $—C_nH_{2n+1}$, $—C_nH_{2n-1}$, $—C_6H_5$, $—CH_2CH_2C_6H_5$, $—CH_2C_6H_5$, $—C_{10}H_7$, or the like. R of the aforementioned $—RSi(R')_n(OA)_{3-n}$ is a chain hydrocarbon group having a carbon number of 1 to 12 (for example, $—C_nH_{2n}$). The aforementioned R' is a chain hydrocarbon group having a carbon number of 1 to 4 (for example, $—C_nH_{2n+1}$). The aforementioned A is H or a chain hydrocarbon group having a carbon number of 1 to 4 (for example, $—CH_3$, $—C_2H_5$, $—CH(CH_3)_2$, $—CH_2CH(CH_3)_2$, and $—C(CH_3)_3$). n is an integer of 0 to 2. At least one, out of all $R_1$s and all $R_2$s, is the aforementioned $—RSi(R')_n(OA)_{3-n}$. Each of $R_1$ and $R_2$ could be identical or could be different.

Preferably, the aforementioned bonding method further includes a step (V) of applying a substance represented by the aforementioned general formula [II] onto the surface of the aforementioned compound (α) after the aforementioned step (X) and yet before the aforementioned step (Y). That is, existence of the polymer represented by the aforementioned general formula [II] on the surface caused the number of —OH groups existing on the surface to be increased, and the adhesiveness to be improved.

In the aforementioned general formula [II], each of X' and Y' is Si or Ti. Z is Al. G is a hydrocarbon group having a carbon number of 1 to 3 (for example, $—CH_3$, $—C_2H_5$, and $—CH=CH_2$), or an alkoxy group having a carbon number of 1 to 3 (for example, $—OCH_3$ and $—OC_2H_5$). B is an alkoxy group having a carbon number of 1 to 3 (for example, $—OCH_3$ and $—OC_2H_5$). Each of n and m is an integer of 0 to 200 (where 2≤n+m≤400). p is an integer of 0 to 100. Preferably, n≠1, m≠1, and p≠1.

Preferably, the aforementioned bonding method further includes a step (U) of applying a compound (β) having an alkoxysilyl group, an alkoxy aluminate group, and/or an alkoxy titanate group onto the surface of the aforementioned compound (α) after the aforementioned step (X) (or aforementioned step (V)) and yet before the aforementioned step (Y). That is, existence of the aforementioned compound (β) on the surface causes the number of —OH groups existing on the surface to be increased. Or, in addition, reactive functional groups are introduced. And, the adhesiveness was improved. Herein, the aforementioned compound (β) is preferably a compound represented by the aforementioned general formulas [T], [III], or [IV].

In the aforementioned general formulas [III] and [IV], each of $R_5$ and $R_7$ is a hydrocarbon group having a carbon number of 1 to 12. $R_6$ is H or a hydrocarbon group having a carbon number of 1 to 10. The aforementioned hydrocarbon group is a chain hydrocarbon group or a cyclic hydrocarbon group. More specifically, the above hydrocarbon group is a saturated aliphatic hydrocarbon group. Or, the above hydrocarbon group is an unsaturated aliphatic hydrocarbon group. Or, the above hydrocarbon group is an aromatic hydrocarbon group. The aforementioned aliphatic hydrocarbon group could be a linear chain hydrocarbon group or a branched chain hydrocarbon group. There are the case in which the aforementioned aromatic hydrocarbon group has a substituent group and the case in which the aforementioned aromatic hydrocarbon group has no substituent group. In addition, there are the case in which each of the aforementioned $R_5$ and $R_7$ has groups such as —NH—, —CO—, —O—, —S—, and —COO— and the case in which it has not. X" is H or a hydrocarbon group having a carbon number of 1 to 10. This hydrocarbon group is a chain hydrocarbon group. More specifically, this hydrocarbon group is a saturated aliphatic hydrocarbon group. Or, this hydrocarbon group is an unsaturated aliphatic hydrocarbon group. These aliphatic hydrocarbon groups have no cyclic group; however, they have a cyclic group as a substitute group in some cases. Y" is an alkyloxy group having a carbon number of 1 to 10. n is an integer of 1 to 3. $M^1$ is H, Li, Na, K, or Cs.

A second present invention is a bonded body (complex). In particular, the second present invention is a bonded body (complex) produced by integrally bonding (chemically bonding) the aforementioned base A and the aforementioned base B with the aforementioned bonding method.

A third present invention is an adhesiveness improver (adhesiveness improvement agent: bondability improving agent). In this specification, literally, the adhesiveness improver is an agent for improving the adhesiveness. It may be also said that to say that the adhesiveness has been improved is identical to saying that a role of the adhesive is played. In this specification, "the adhesiveness improver" is employed as a terminology also containing the meaning of "the adhesive". The aforementioned adhesiveness improver (adhesive) is preferably applied onto the surface of the base A configured by employing a polymer.

The aforementioned adhesiveness improver (adhesive) includes a compound (α) having at least one OH group or at least one OH yielding group, at least one azide group, and at least one triazine ring per molecule. Preferably, the compound (α) includes at least one alkoxysilyl group (the case in which an alkoxy group in the aforementioned alkoxysilyl group is the OH group is also included) and at least one azide group per molecule. This compound (α) preferably has a structure in which at least one azide group and at least one alkoxysilyl group are directly or indirectly bonded to triazine (among them, 1,3,5-triazine). Preferably, this compound (α) is a compound represented by the aforementioned general formula [I]. More preferably, this compound (α) is a compound represented by the aforementioned general formula [Io]. Yet more preferably, this compound (α) is a compound represented by the aforementioned general formula [Ia] or [Ib].

A fourth present invention is a surface modification method. Particularly, the fourth present invention is a surface modification method of modifying properties of the base surface. The aforementioned surface modification method includes a step of applying a surface modifying agent onto the surface of the base. The aforementioned surface modifying agent includes a compound (α) having at least one OH group or at least one OH yielding group, at least one azide group, and at least one triazine ring per molecule. The compound (α) preferably includes at least one alkoxysilyl group (the case in which an alkoxy group in the aforementioned alkoxysilyl group is the OH group is also included), at least one azide group, and at least one triazine ring per molecule. This compound (α) preferably has a structure in which at least one azide group and at least one alkoxysilyl group are directly or indirectly bonded to triazine (among them, 1,3,5-triazine). Preferably, this compound (α) is a compound represented by the aforementioned general formula [I]. More preferably, this compound (α) is a compound represented by the aforementioned general formula [Io]. Yet more preferably, this compound (α) is a compound represented by the aforementioned general formula [Ia] or [Ib].

The aforementioned surface modification method preferably includes a step of radiating light after the aforementioned surface modifying agent is applied. The aforementioned light irradiation step is a step of performing photographic exposure in a predetermined pattern. This surface modification method is performed in accordance with the aforementioned bonding method. Thus, when this surface modification method is performed, the status in which the alkoxysilyl group (or the OH group) exists on the surface is obtained. This modifies the surface.

A fifth present invention is a base subjected to the surface modification of the present invention. That is, the fifth present invention is a base for which the surface modification method has been performed.

A sixth present invention is a surface modifying agent. This surface modifying agent includes a compound (α) having at least one OH group or at least one OH yielding group, at least one azide group, and at least one triazine ring per molecule. Preferably, the compound (α) includes at least one alkoxysilyl group (the case in which an alkoxy group in the aforementioned alkoxysilyl group is the OH group is also included) and at least one azide group per molecule. This compound (α) preferably has a structure in which at least one azide group and at least one alkoxysilyl group are directly or indirectly bonded to triazine (among them, 1,3,5-triazine). Preferably, this compound (α) is a compound represented by the aforementioned general formula [I]. More preferably, this compound (α) is a compound represented by the aforementioned general formula [Io]. Yet more preferably, this compound (α) is a compound represented by the aforementioned general formula [Ia] or [Ib]. This surface modifying agent is applied in accordance with the aforementioned adhesiveness improver.

A seventh present invention is a novel compound. This novel compound is a compound represented by the aforementioned general formula [Io]. Particularly, this novel compound is a compound represented by the aforementioned general formula [Ia]. Or, this novel compound is a compound represented by the aforementioned general formula [Ib].

The present invention makes it possible to cause the compound (α) represented by, for example, the aforementioned general formulas [I], [Io], [Ia], or [Ib] and an amplifying agent (for example, the compound represented by the general formulas [II], [T], [III], or [IV]) to coexist on the surface of the base A. And, thereafter, light (ultraviolet rays) is radiated. Or, the heating may be performed prior to the aforementioned light irradiation. In the present invention, the compound (α) represented by the aforementioned general formulas [I], [Io], [Ia], or [Ib] is applied onto the surface of the base A. Or, the amplifying agent (for example, the compound represented by the general formulas [II], [T], [III], or [IV]) is applied. And, the light irradiation is performed (or, the light irradiation after heating). Thereafter, it is preferably immersed into an acid solution or an alkaline solution.

In the present invention, a silane coupling agent having an alkoxysilyl group and a benzo phenone-based photosensitizer and the like may be also used together with, or instead of the aforementioned amplifying agent.

In the present invention, the polymer (high polymerized material) was listed as a constituent material of the base A. The base B was not exemplified so far. As a constituent material of the base B, metal materials, ceramic materials, and organic materials can be listed. The technology similar to the surface modification technology of the base A may be adopted.

Besides, the surface modification using silane coupling agents (for example, a vinyl group-based silane coupling agent, an allyl group-based silane coupling agent, a malonic acid anhydride-based silane coupling agent, a halogenoalkyl-based silane coupling agent, an amine-based silane coupling agent, an epoxy-based silane coupling agent, an acrylate-based silane coupling agent, a methacrylate-based silane coupling agent, a phosphate-based silane coupling agent, or a sulfur-based silane coupling agent) may be performed. For example, the base B is immersed into a solution containing the aforementioned coupling agents (0.001 to 2 wt %). The temperature at the time of the immersion is preferably 20 to 200° C. The time is preferably 1 to 60 min. At this time, preferably, the base surface is previously subjected to the cleaning process.

In accordance with the present invention, for example, alkoxysilyl groups are introduced into the base A surface due to the chemical reaction (bonding) between the azide group of the compound (α) and the base A. And, the alkoxysilyl group is modified into the OH group. As a result, the adhesiveness with the base B comprised of various types of the materials was improved. That is, the base A and the base B are linked via the chemical bonding, and the bonding (adhesion) strength thereof is strong. Moreover, a necessity for the corona discharge treatment and the plasma treatment was eliminated. That is, the OH groups were introduced into the base A surface in a simplified manner even though such treatments were not performed. Thus, workability is excellent. And yet, the surface layer of the base A is hardly decomposed.

The aforementioned compound (α) is applied onto the base A surface. Thereafter, light is radiated. At this time, the chemical reaction occurs between the aforementioned compound (α) and the base A. As a result, the aforementioned compound (α) and the base A are bonded to each other. The base A is configured of a polymer. As the aforementioned polymer, curing resin (for example, thermosetting resin, photo-curing resin and electron-beam curing resin) and thermoplastic resin can be listed. Fiber-reinforced resin as well can be listed. Rubber (vulcanized rubber) can be also listed. In addition to these, the material having a coating film containing a polymer formed on the surface thereof may be used.

By the way, it is known that the azide compound is a crosslinking agent. That is, irradiation of a composite containing the azide compound with the ultraviolet rays allows the polymer having a crosslinking structure to be obtained. However, it was not known whether or not the azide group was chemically bonded to the polymer (molecular chains of the polymer surface) when the ultraviolet rays were radiated in a situation in which the azide compound existed on the polymer surface (a situation in which they were not being mixed).

The following experiment was tried by this inventor. The aforementioned compound (α) (in particular, the compounds represented by the aforementioned general formulas [I], [Io], [Ia], and [Ib]) was applied onto the polymer surface. Thereafter, light was radiated. As a result, the chemical reaction occurred between the azide group and the polymer (molecular chains of the polymer surface). That is, the chemical bonding occurred between the aforementioned compound (α) and the aforementioned polymer. And, it became clear that the alkoxysilyl group was present on the polymer surface. This fact was not able to be imaged from the conventional knowledge. And, the base A subjected to a surface modification with the alkoxysilyl group was treated with the compounds represented by the aforementioned general formulas [II], [T], [III], and [IV]) and silane coupling agents. With this, the adhesiveness was improved all the more.

Hereinafter, the present invention will be explained from a viewpoint different from the above-mentioned viewpoint.

[Compound (α) (Adhesiveness Improver (Adhesive): Molecular Adhesive)]

As apparently from the above-mentioned explanation, the adhesiveness improver (aforementioned compound (α)) of the present invention is expressed as a molecular adhesive.

The aforementioned compound (α) has an alkoxysilyl group and an azide group. The aforementioned compound (α) further has a triazine ring. Preferably, the azide group is directly bonded to the triazine ring (C atom). The number of the azide groups that have been bonded to the triazine ring is, for example, one or two. Preferably, the OH group or the OH yielding group (for example, alkoxysilyl group) is indirectly bonded to the triazine ring (C atom) via a spacer (for example, an amino group, an oxy group, and/or a hydrocarbon group). The number of the alkoxysilyl groups indirectly bonded to the triazine ring is one, or two or more.

It has become clear that the azide group bonded to the triazine ring (electron localization conjugated system) is high in energy of resolution into nitrene. Thus, an influence by near ultraviolet rays and visible light hardly occur. For this, workability of exposure of the ultraviolet rays is improved. It has become clear that the nitrene bonded to the triazine ring is more stable as compared with the nitrene that has not been bonded. It has become clear that the bonding of the nitrene partners is suppressed. It has become clear that hydrogen abstraction activity for the C—H bonds and addition activity for the unsaturated bonds are strengthened. That is, it has become clear that the effective reaction is enabled with a small amount of the photographic exposure.

The aforementioned alkoxysilyl group has been bonded to the triazine ring (electron localization conjugated system) via the spacer (for example, an amino group, an oxy group, and/or a hydrocarbon group). For this, when the aforementioned compound (α) is bonded to the polymer surface, an entropy effect for generating the chemical bond is enhanced in a contact with various types of the materials. An enhancement in the entropy effect causes a frequency factor term in an interface reaction to be increased after contact between the polymer (the aforementioned base A) and various types of the materials (the aforementioned base B). As a result, an opportunity of the interface reaction is increased. The length of the aforementioned spacer is reflected into an increase in the frequency factor in the interface reaction. When the length of the spacer is too long, the cost becomes higher. And yet, a reduction in an absorption quantity of the molecular adhesive occurs. Thus, the spacer having an appropriate length is desirable. The compounds represented by the aforementioned general formulas [Io], [Ia], and [Ib] were desirable from such a viewpoint.

From a viewpoint of an increase in the frequency factor term in the interface reaction, the more the number of the alkoxysilyl groups and azide groups existing per molecule is, the more preferable it will be. However, its number as well is restrained from a viewpoint of the cost etc. That is, the compounds represented by the aforementioned general formulas [Io], [Ia], and [Ib] were desirable from such a viewpoint.

The alkoxysilyl group in the aforementioned general formulas [Io], [Ia], and [Ib] is an OH yielding group (OH precursor) in almost cases. So as to modify the OH yielding group into the OH group, it is treated with water (neutral water, acid water, and alkaline water). In addition hereto, the corona discharge treatment and the plasma treatment are thinkable. However, the water treatment is desirable.

The compound (α) was synthesized along with the following reaction formula.

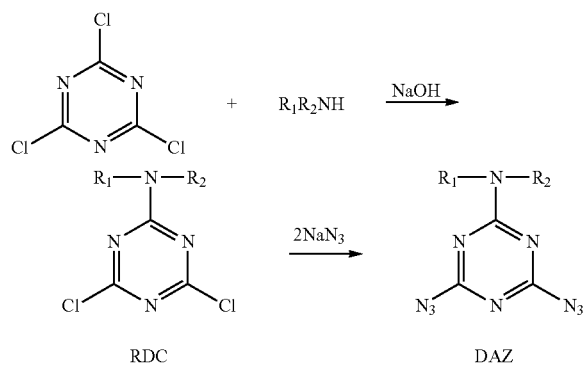

An acetone (or alcohol (for example, methanol, ethanol, etc.)) solution of an amino compound (for example, amino alcohol) containing the hydroxyl group was dripped into an acetone solution of cyanuric chloride under the stirring. The temperature at this time is 0 to 10° C. Thereafter, a NaOH aqueous solution was dripped. With this, RDC was obtained. A DMF aqueous solution of NaN₃ was dripped into a dimethyl formamide (DMF) (or alcohol) solution of this RDC. The temperature at this time is 40 to 60° C. With this, DAZ was obtained.

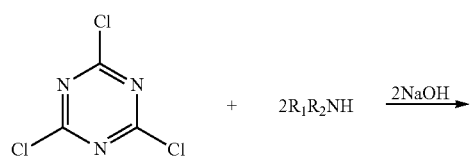

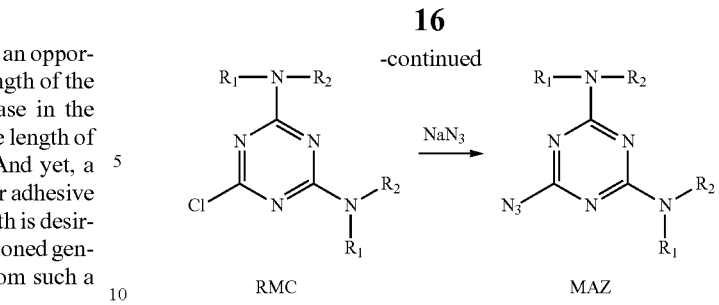

A tetrahydrofuran (THF) (or alcohol (for example, methanol, ethanol, etc.)) solution of the amino compound (for example, alkoxysilyl alkylamine) containing the hydroxyl group was dripped into a THF (or alcohol (for example, methanol, ethanol, etc.)) solution of cyanuric chloride under the stirring. The temperature at this time is 0 to 50° C. Thereafter, a NaOH aqueous solution was dripped. With this, RMC was obtained. A DMF (or alcohol) aqueous solution of NaN₃ was dripped into a DMF (or alcohol) solution of this RMC. The temperature at this time is 50 to 70° C. With this, MAZ was obtained.

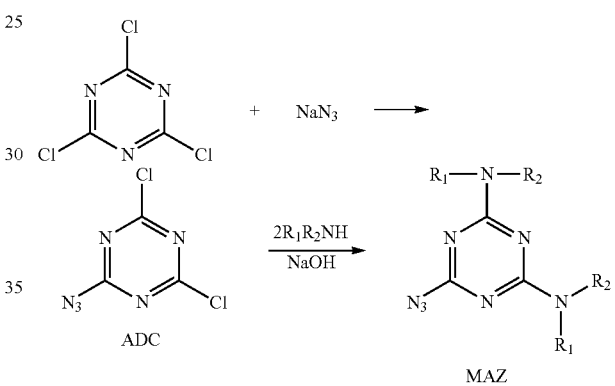

A NaN₃ aqueous solution was dripped into an acetone (or alcohol (for example, methanol, ethanol, etc.)) solution of cyanuric chloride under the stirring. The temperature at this time is 0 to 5° C. With this, ADC was obtained. The amino compound solution containing the hydroxyl group was dripped into an acetone (or alcohol) solution of this ADC. The temperature at this time is 40 to 60° C. With this, MAZ was obtained.

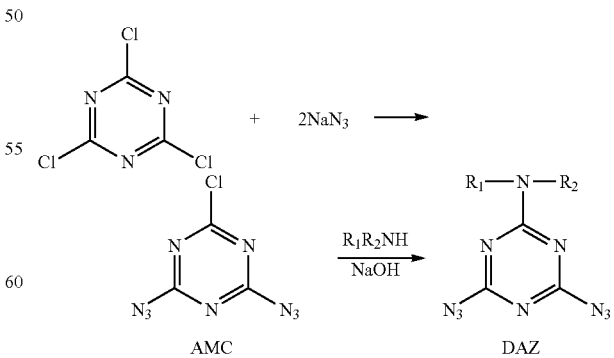

A NaN₃ aqueous solution was dripped into an acetone (or alcohol (for example, methanol, ethanol, etc.)) solution of cyanuric chloride under the stirring. The temperature at this time is 0 to 60° C. With this, AMC was obtained. The amino compound solution containing the hydroxyl group was dripped into an acetone (or alcohol) solution of this AMC. The temperature at this time is 0 to 10° C. With this, DAZ was obtained.

The molecular adhesive of the present invention (compound α) is triazine compounds having an alkoxysilyl group and an azide group. Such a compound is preferably the compounds represented by the aforementioned general formulas [I], [Io], [Ia], and [Ib]. As the compound of this type, for example, 6-azide-2,4-bis(ethanolamino)-1,3,5-triazine, 6-azide-2,4-bis(hexanolamino)-1,3,5-triazine, 6-azide-2,4-bis(decanolamino)-1,3,5-triazine, 6-azide-2,4-bis(3,4-bishydroxyphenyl)amino)-1,3,5-triazine, 6-azide-2,4-bis(2,2-dihydroxymethyl)ethylamino-1,3,5-triazine, 6-azide-2,4-bis(tris methanol methyl)methylamino-1,3,5-triazine, 6-azide-2,4-(1,2-dihydroxypropyl)amino-1,3,5-triazine, 6-azide-2,4-bis(3-triethoxysilyl)propylamino-1,3,5-triazine (TE-MAZ), 6-azide-2,4-bis(3-methylethylketoxyminosilyl)propylamino-1,3,5-triazine, 6-azide-2,4-bis(3-methylethylketoxyminosilyl)propylamino-1,3,5-triazine, 6-azide-2,4-bis(3-triisopropoxysilyl)propylamino-1,3,5-triazine, 6-azide-2,4-bis(3-triacetoxysilyl)propylamino-1,3,5-triazine, 6-azide-2,4-bis(3-triisopropoxysilyl)propylamino-1,3,5-triazine, 6-azide-2,4-bis(3-triisopropoxysilyl)propylamino-1,3,5-triazine, 6-azide-2,4-bis(3-tribenzoxysilyl)propylamino-1,3,5-triazine, 6-azide-2,4-bis(diethanolamino)-1,3,5-triazine, 6-azide-2,4-bis(dihexanolamino)-1,3,5-triazine, 6-azide-2,4-bis(didecanolamino)-1,3,5-triazine, 6-azide-2,4-bis(3-triethoxysilylpropyl)amino-1,3,5-triazine, 6-azide-2,4-bis(6-triethoxysilylhexyl)amino-1,3,5-triazine, 6-azide-2,4-bis(10-triethoxysilyldodecyl)amino-1,3,5-triazine, 2,4-diazide-6-(N,N-diethanol)amino-1,3,5-triazine (DEA-DAZ), 2,4-diazide-6-(N,N-didecanol)amino-1,3,5-triazine, 2,4-diazide-6-(3,4-bishydroxyphenyl)amino-1,3,5-triazine, 2,4-diazide-6-(2,2-dihydroxymethyl)ethylamino-1,3,5-triazine, 2,4-diazide-6-(tris methanol methyl)methylamino-1,3,5-triazine, 2,4-diazide-6-(1,2-dihydroxypropyl)amino-1,3,5-triazine, 2,4-diazide-6-(3-triethoxysilylpropyl)amino-1,3,5-triazine (TE-DAZ), 2,4-diazide-6-bis(3-methylethylketoxyminosilyl)propylamino-1,3,5-triazine, 2,4-diazide-6-bis(3-methylethylketoxyminosilyl)propylamino-1,3,5-triazine, 2,4-diazide-6-(3-triisopropoxysilyl)propylamino-1,3,5-triazine, 2,4-diazide-6-(3-triacetoxysilyl)propylamino-1,3,5-triazine, 2,4-diazide-6-(3-triisopropoxysilyl)propylamino-1,3,5-triazine, 2,4-diazide-6-(3-triisopropoxysilyl)propylamino-1,3,5-triazine, 2,4-diazide-6-(3-tribenzoxysilyl)propylamino-1,3,5-triazine, 2,4-diazide-6-bis(dihydroxyethyl)amino-1,3,5-triazine, 2,4-diazide-6-(N,N-dihexanol)amino-1,3,5-triazine, 2,4-diazide-6-(N,N-didecanol)amino-1,3,5-triazine, 2,4-diazide-6-(N,N-bis(3-triethoxysilylpropyl)amino-1,3,5-triazine (BTE-DAZ), 2,4-diazide-6-(N,N-bis(6-triethoxysilylhexyl)amino-1,3,5-triazine, 6-(11-triethoxysilylundecyl)amino-1,3,5-triazine-2,4-diazide (TEU-DAZ), 6-(3-diethoxymethylsilylpropyl)amino-1,3,5-triazine-2,4-diazide (DEM-DAZ), 6-(4-triethoxysilylbutyl)amino-1,3,5-triazine-2,4-diazide (TEB-DAZ), and the like can be listed.

[Base A (Polymer)]

The base A is configured of a polymer (resin). The aforementioned polymer has, for example, a C—H bond or a Si—O bond. In particular, the aforementioned polymer has the C—H bond. The aforementioned polymer is curing resin (for example, thermosetting resin, photo-curing resin and electron-beam curing resin). Or, the aforementioned polymer is thermoplastic resin. Or, the aforementioned polymer is fiber-reinforced resin. Or, the aforementioned polymer is rubber and vulcanized rubber. In addition to these, the material having a coating film containing a polymer (binder resin) formed on the surface thereof may be used. The aforementioned polymer has a two-dimensional linear structure. Or, the aforementioned polymer has a three-dimensional net structure. The shape of the base A is governed by applications. For example, the shapes such as a film shape, a sheet shape, a plate shape, a column shape, a bar shape, a frame shape, a box shape, a fiber shape, a yarn shape, a cloth shape, an unwoven cloth shape and a foam shape can be listed.

As specific examples of the aforementioned polymer etc., for example, cellulose and its derivatives, hydroxyethyl cellulose, starch, cellulose diacetate, surface saponified vinyl acetate resin, low-density polyethylene, high-density polyethylene, polypropylene, ethylene-propylene copolymer, petroleum resin, polystyrene, syndiotactic-polystyrene, styrene copolymer, chroman-indene resin, terpene resin, styrene-divinyl benzen copolymer, acrylonitrile-butadiene-styrene copolymer resin, polymethyl acrylate, polyethyl acrylate, polyacryl nitrile, polymethyl acrylate, polymethyl methacrylate, polyethyl methacrylate, polycyano acrylate, polyvinyl acetate, ethylene-vinyl acetate copolymer resin, polyvinyl alcohol, polyvinyl formal, polyvinyl acetal, vinyl acetate copolymer, polyvinyl chloride, vinyl chloride-vinyl acetate copolymer, vinyl chloride-ethylene copolymer, poly(vinyliden fluoride), vinyliden fluoride-ethylene copolymer, vinyliden fluoride-propylene copolymer, poly 1,4-transpolybutadiene, poly 1,2-transpolybutadiene, polyoxy methylene, polyethylene glycol, polypropylene glycol, phenol-formalin resin, cresol-formalin resin, resorcinol resin, melamine resin, xylene resin, toluene resin, glyptal resin, modified glyptal resin, polyethylene terephthalate, polybutylene terephthalate, unsaturated polyester resin, polyester acrylate, allylester resin, polycarbonate, 6-nylon, 6',6-nylon, 6',10-nylon, polyimide, polyamide, polybenzimidazole, polybenzoxazole, polybenzothiazole, polyamideimide, silicon resin, addition-curable type silicone rubber, polymerization-curable type silicone rubber, condensation-curable type silicone rubber, addition-curable type silicone resin, furan resin, polyurethane resin, epoxy resin, polyphenylene oxide, polydimethylphenylene oxide, blend polymers (polymer alloys) of polyphenylene oxide or polydimethylphenylene oxide and triallylisocyanuric acid, blend polymers (polymer alloys) of polyphenylene oxide or polydimethylphenylene oxide and triallylisocyanurate peroxide, polyxylene, polyphenylene sulfide, polycycloolefin, polysulfone, polyethersulfone, polyetheretherketone, polyimide, liquid crystal resin (LCP), natural rubber, 1,4-cisbutadiene rubber, isoprene rubber, polychloroprene, styrene-butadiene copolymer rubber, hydrogenated styrene-butadiene copolymer rubber, acrylnitrile-butadiene copolymer rubber, hydrogenated acrylnitrile-butadiene copolymer rubber, polybutene rubber, polyisobutylene rubber, ethylene-propylene rubber, ethylene-propylene-diene rubber, ethylene oxides-epichlorohydrin copolymer rubber, chlorinated polyethylene rubber, chlorosulfonated polyethylene rubber, alkylated chlorosulfonated polyethylene rubber, chloroprene rubber, chlorinated acryl rubber, brominated acryl rubber, flourine rubber, epichlorohydrin copolymer rubber, chlorinated ethylene-propylene rubber, chlorinated buthyl rubber, brominated buthyl rubber, tetrafluoroethylene, hexafluoropropylene, homopolymer rubber such as vinylidene fluoride and tetrafluoroethylene, and copolymer rubber and terpolymer rubber thereof, ethylene-tetrafluoroethylene copolymer rubber, propylene-tetrafluoroethylene copolymer rubber, ethyleneacryl rubber, peroxide type silicone rubber, addition type silicone rubber, condensation type silicone rubber, epoxy rubber, urethane rubber, elastomers having unsaturated groups at both terminals, and the like can be listed.

The aforementioned base A (polymer) includes various kinds of additives (for example, crosslinking agents, crosslinking accelerators, crosslinking assistants, radical initiators, cation initiators, photopolymerization initiators, scorch retarders, stabilizers, antioxidants, ultraviolet ray inhibitors, fillers, reinforcers, plasticizers, softeners, colorants, and viscosity modifiers) according to a necessity.

The aforementioned polymer having the three-dimensional net structure is obtained by subjecting to heating or light irradiation a composite obtained by, for example, adding the crosslinking agent (in addition, the crosslinking accelerator and the crosslinking assistant) to the aforementioned two-dimensional linear polymer. Or, the aforementioned polymer is obtained by subjecting to heating or light irradiation a composite obtained by, for example, adding the crosslinking agent (in addition, the crosslinking accelerator and the crosslinking assistant) to a predetermine monomer (for example, a low molecular monomer having a vinyl group, an acrylate group, a methacrylate group, an epoxy group, an isocyanate group, or an oxetane group of which the number is one, or two or more per molecule).

As the aforementioned monomers, for example, a urethane acrylate-based, an epoxy acrylate-based, an ester acrylate-based, an acrylate-based, an epoxy-based, and a vinyl ether-based monomers can be listed. Specifically, acrylates (for example, ethylene glycol di(metha)acrylate, propylene glycol di(metha)acrylate, polyethylene glycol di(metha)acrylate, 1,4-butanediol di(metha)acrylate, 1,6-hexanediol di(metha)acrylate, trimethylolpropane tri(metha)acrylate, pentaerythritol tetra(metha)acrylate, epoxy(metha)acrylate obtained by an addition reaction with (metha)acrylic acid, polyurethane(metha)acrylate obtained by a reaction with 2-hydroxyethyl(metha)acrylate, diol, and diisocyanate, polyester(metha)acrylate polyester acrylate obtained by a reaction with (metha) acrylic acid, polycarboxylic acid, and polyol, urethane acrylate, epoxy acrylate, polyether acrylate, and polyol acrylate), and methacrylates (for example, polyester methacrylate, urethane methacrylate, epoxy methacrylate, polyether methacrylate, and polyol methacrylate) can be listed. In addition hereto, n-alkyl acrylate, propyl acrylate, i-butyl acrylate, t-butyl acrylate, cyclohexyl acrylate, β-hydroxyethyl acrylate, diethylene glycol acrylate, polyethylene glycol acrylate, β-hydroxypropyl acrylate, glycidyl acrylate, ethylene glycol diacrylate, diethylene glycol diacrylate, triethylene glycol diacrylate, polyethylene glycol diacrylate, dialkylamino ethyl acrylate, 2-cyanoethyl acrylate, β-ethoxyethyl acrylate, aryl acrylate, benzoyloxyethyl acrylate, benzyl acrylate, phenoxyethyl acrylate, phenoxydiethylene glycol acrylate, 2-hydroxy-3-phenoxypropyl acrylate, tetrahydrofurfuryl acrylate, addition product acrylates of tetrahydrofurfuryl alcohol and ε-caprolactone, bornyl acrylate, dicyclopentenyloxyethyl acrylate, 1,4-butanediol diacrylate, 1,6-hexanediol diacrylate, 1,9-nonandiol diacrylate, neopentyl glycol diacrylate, triethylene glycol diacrylate, tetraethylene glycol diacrylate, polyethylene glycol diacrylate, tripropylene glycol diacrylate, hydroxypivalic acid neopentyl glycol diacrylate, acetal glycol diacrylate, addition product diacrylate of hydroxypivalic acid neopentyl glycol and ε-caprolactone, trimethylolpropane triacrylate, trimethylolpropane.polyethoxylate.triacrylate, trimethylolpropane.polyproxylate.triacrylate, pentaerythritol triacrylate, dipentaerythritol hexaacrylate, addition product hexaacrylates of dipentaerythritol and ε-caprolactone, acryloxyethyl phosphate, fluoroalkyl acrylate, sulfopropyl acrylate, methyl methacrylate, ethyl methacrylate, propyl methacrylate, i-propyl methacrylate, butyl methacrylate, isobutyl methacrylate, sec-butyl methacrylate, t-butyl methacrylate, hexyl methacrylate, octyl methacrylate, i-octyl methacrylate, 2-ethylhexyl methacrylate, decyl methacrylate, lauryl methacrylate, stearyl methacrylate, 2-hydroxyethyl methacrylate, 2-hydroxypropyl methacrylate, 2-dimethylamino ethyl methacrylate, 2-diethylamino ethyl methacrylate, 2-t-butylamino ethyl methacrylate, glycidyl methacrylate, allyl methacrylate, cyclohexyl methacrylate, phenyl methacrylate, nonylphenyl methacrylate, benzyl methacrylate, dicyclopentenyl methacrylate, bornyl methacrylate, 1,4-butanediol dimethacrylate, 1,3-butanediol dimethacrylate, ethylene glycol dimethacrylate, diethylene glycol dimethacrylate, triethylene glycol dimethacrylate, tetraethylene glycol dimethacrylate, polyethylene glycol dimethacrylate, neopentyl glycol dimethacrylate, 1,6-hexanediol dimethacrylate, dipropylene glycol dimethacrylate, trimethylolpropane trimethacrylate, glycerol methacrylate, methacryloxyethyl phosphate, bis.methacryloxyethyl phosphate, arone oxetane, di[1-ethyl(3-oxetanyl)] methylether, 3-ethyl-3-(hexyloxymethyl) oxetane, xylylene dioxetane, phenyl oxetane, oxetanyl silsesquioxane, 3-ethyl-3-(heptyloxymethyl) oxetane, 3-ethyl-3-(2-ethyl hexyloxymethyl) oxetane, 3-ethyl-3-(octyloxymethyl) oxetane, 3-ethyl-3-(dodecyloxymethyl) oxetane, bisphenol A type epoxy monomer, bisphenol F type epoxy monomer, novolac-type epoxy monomer, toluene diisocyanate, and the like can be listed.

Various types are used for the aforementioned polymerization initiator, crosslinking agent, crosslinking accelerator, and crosslinking assistant. For example, peroxides, cation polymerization initiators, photopolymerization initiators, sulfur, sulfur-based crosslinking accelerators, polyol-based crosslinking agents, polyamine-based crosslinking agents, polythiol-based crosslinking agents, acrylate-based crosslinking assistants, methacrylate-based crosslinking assistants, and allyl-based crosslinking assistants can be listed. Specifically, for example, azobisisobutyronitrile, benzo phenon, Michler's ketone, benzoin isopropyl ether, chlorothioxanthone, isopropylthioxanthone, benzyldimethyl ketal, acetophenonediethyl ketal, α-hydroxycyclohexyl phenylketone, and 2-hydroxy-2-methyl-phenylpropane can be listed. Acetophenone derivative compounds (for example, 4-(2-hydroxyethoxy)phenyl(2-hydroxy-2-propyl)ketone, α-hydroxy-α,α'-dimethylacetophenone, methoxyacetophenone and 2,2-dimethoxy-2-phenylacetophenone) can be also listed. Benzoin ether-based compounds (for example, benzoin ethyl ether and benzoin proply ether) can be also listed. Ketal derivative compounds such as benzyldimethyl ketal can be also listed. Halogenated ketone, acylphosphine oxide, acylphosphonate, bis(2,6-dimethoxybenzoyl)-2,4,4-trimethylpentyl phosphine oxide, phenyl dimethyl sulfonium chloride, and triaryl sulfonium hexafluoro phosphate can be also listed. Triazinedithiol-based crosslinking agents, resin crosslinking agents, polyol crosslinking agents, H-terminal siloxane-based crosslinking agents, and silanol condensation type crosslinking agents can be listed. Dibenzothiazoyl disulfide, 4-morpholino dithio benzothiazole, N-cyclohexyl-2-benzothiazoyl sulfenamide, N-t-butyl-2-benzothiazoyl sulfenamide, N-oxydiethylene-2-benzothiazoyl sulfenamide, N-diisopropyl-2-benzothiazoyl sulfenamide, N-dicyclohexyl-2-benzothiazoyl sulfenamide, tetramethyl thiuram disulfide, tetraethyl thiuram disulfide, tetrabutyl thiuram disulfide, tetraoctyl thiuram disulfide, amines, hexamethylene tetramine, saligen, quaternary ammonium salts, phosphonium salts, dialkyl tin organic acid salts, titanate, polyethylene glycol, chloroplatinic acid, zinc oxide, magnesium oxide, calcium oxide, barium oxide, aluminum oxide, calcium hydroxide, tin oxide, iron oxide, calcium hydroxide, calcium carbonate, magnesium carbonate, fatty acid sodium, calcium octylate, potassium isooctylate, potassium butoxide, cesium octylate, potassium isostearate, polyethylene glycol, polypropylene glycol, hexanediol, cyclohexanediol, dodecanediol, hexamethylene diamine, dodecane diamine, polyethylene glycol containing diamino at terminals, polypropylene glycol containing diamino at terminals, benzenedithiol, hexanedithiol, 1,10-decanedithiol, 1,12-dodecanedithiol, polyethylene glycol diacrylate, polyethylene glycol dimethacrylate, polypropylene glycol diacrylate, polypropylene glycol dimethacrylate, diallyl ether, triallyl isocyanurate, and triallyl cyanurate can be also listed.

The base A made of the polymer having the two-dimensional linear structure (thermoplastic resin, un-crosslinked rubber) and the polymer having the three-dimensional net structure (heat-curable resin, crosslinked rubber) each of which is a high polymerized material is obtained by performing a roll sheeting work, a calendar rolling work, a pressing work, an extruding work, or an injection molding work for a composite obtained by adding 0.1 to 20 parts by weight of the crosslinking agent, 0.1 to 20 parts by weight of the crosslinking accelerator, and 0.1 to 20 parts by weight of the crosslinking assistant to 100 parts by weight of the two-dimensional linear structure polymer (or monomer) under conditions of a temperature of 20 to 350° C. and a working time of 0.1 second to 200 minutes. However, an adding amount of the crosslinking agent etc., the working temperature, and the working time differ depending on special features of working machines. Additionally, when the polymer having the two-dimensional linear structure or thermoplastic resin is employed, the crosslinking agent may not be added.

When the base A is configured of the photo-curing resin, UV devices (for example, high-pressure mercury UV lamps, low-pressure mercury UV lamps, fluorescence type UV lamps (short ARC xenon lamps and chemical lamps) and metal halide lamps) are used, and the base A is obtained by irradiating the composite with the ultraviolet rays having a wavelength of 200 to 450 nm in a desired environment (for example, in the air, in a nitrogen atmosphere, in an argon atmosphere, or under depressurization).

The vulcanized rubber is obtained by keeping the composite containing one kind, or two kinds or more of elastomers selected from a group of linear copolymers of which a glass transition temperature is equal to less than −20° C., and the additives (for example, the crosslinking agent, the crosslinking accelerator and the like) for 0.1 to 1200 minutes and at a temperature of 0 to 300° C. The addition type silicone rubber, the condensation type silicone rubber and the like are obtained with long-time heating at a low temperature in some cases. In general, the temperature is 60 to 180° C. in many cases.

The aforementioned base A contains an appropriate amount of various types of fillers and reinforcers according to a necessity. For example, various types of carbon blacks, calcium carbonate, talc, clay, kaolin, glass, wet silica, and dry silica are contained according to a necessity. Rayon, nylon, polyester, vinylon, steel, Kevlar fibers, carbon fibers, and glass fibers, and clothes are contained according to a necessity. Metal particles (copper, nickel, silver, gold, tin and the like) are contained according to a necessity. Carbon particles are contained according to a necessity. Conductive materials are contained according to a necessity. Heat-transfer materials such as alumina, silicon nitride, alumina nitride, silicon carbide, and diamond are contained according to a necessity. The containing amount is 200 parts or less by weight per 100 parts by weight of the polymer. In general, the containing amount is 100 parts or less by weight.

The aforementioned base A contains an appropriate amount of stabilizers according a necessity. The stabilizers are, for example, antioxidants or ultraviolet ray absorbers. For example, the stabilizers are amine.ketone-based condensation products such as poly(2,2,4-trimethyl-1,2-dihydroquinoline) and 6-ethoxy-1,2-dihydro-2,2,4-trimethylquinoline. The stabilizers are secondary aromatic amine compounds such as octyldiphenylamine, 4,4-bis($\alpha,\alpha$-dimethylbenzyl)diphenylamine, N,N-diphenyl-p-phenylenediamine, N-phenyl-N'-isopropyl-p-phenylenediamine, and N-phenyl-N'-isopropyl-1,3-dimethylbutyl-p-phenylenediamine.

Monophenol-based or bisphenol-based compounds such as styrenated phenol, 2,6-di-t-butyl-4-phenol, 2-t-butyl-6-(3-t-butyl-2-hydroxy-5-methylbenzyl)-4-methylphenylacrylate, 2,2-methylenebis(4-methyl-6-t-butylphenol), 4,4-thiobis(3-methyl-6-t-butylphenol)2,5-di-t-butylhydroquinone. Sulfuric or phosphorus compounds such as 2-mercapto benzimidazole, 2-zinc mercapto benzimidazole, nickel dimethyl dithio carbamate, 1,3-bis(dimethylaminopropyl)thiourea, dilauryl-3,3-thiodipropionate, and tris(nonylated phenyl) phosphite. The containing amount is 30 parts or less by weight per 100 parts by weight of the polymer. In general, the containing amount is 0.5 to 5 parts by weight.

The aforementioned base A contains an appropriate amount of the following compounds according to a necessity. For example, the ultraviolet ray absorbers such as 2-ethylhexyl paramethoxy cinnamate (octyl), 2-ethylhexyl paradimethylamino benzoate (octyl), oxybensone(benzophenone3), 2-ethylhexyl salicylate (octyl), 4-tert-butyl-4-methoxybenzoylmethane, benzoate-based stabilizers, and hindered amine-based light stabilizers are contained. The containing amount is 10 parts or less by weight per 100 parts by weight of the polymer. In general, the containing amount is 0.1 to 2 parts by weight.

The aforementioned base A contains an appropriate amount of softeners, plasticizers, processing aids, viscosity modifies and colorants according to a necessity, respectively.

[Base B]

The base B to be bonded (adhesion: adhesion by the chemical bonding) to the aforementioned base A (polymer) is configured of metals, ceramics, or organic materials.

No special limit is put to the aforementioned metals. The aforementioned metal is a single metal or an alloy. For example, Be, Mg, Ca, St, Ba, Ra, Sc, It, Ti, Zr, V, Nb, Ta, Cr, Mo, W, Mn, Fe, Co, rhodium, Ir, Ni, palladium, Pt, Cu, Ag, Au, Zn, Cd, Hg, Al, Ge, Sn, Pb, An, Bi, neodymium, and the like can be listed. An iron alloy, a copper alloy, an aluminum alloy, a magnesium alloy, a zinc alloy, a tin alloy, a nickel alloy, a gold alloy, a silver alloy, a platinum alloy, a palladium alloy, a lead alloy, a titanium alloy, a cadmium alloy, a zirconium alloy, a cobalt alloy, a chromium alloy, a molybdenum alloy, a tungsten alloy, a manganese alloy, ferrite stainless steel, martensite-based stainless steel, austenite-based stainless steel, precipitation-hardened stainless steel, a nickel-titanium alloy, an iron-manganese-titanium alloy, a super-elastic alloy (nickel-titanium alloy), and the like can be listed. Besides, the aforementioned metals could be a functional metal, an amorphous metal, a fiber-reinforced metal, a shape memory alloy, and a super-elastic alloy. The shape thereof may be identical to that of the base A, and may be different.

No special limit is also put to the aforementioned ceramics. As ceramics, for example, oxides of the aforementioned metals, china and porcelain, glass, cement, plaster, and the like can be listed. Enamel etc. may be used. Diamonds may be used. Metallic oxides such as alumina, mullite, zirconia, and zinc oxide may be used. Hydroxides such as hydroxyapatite may be used. Carbides such as silicon carbide may be used. Carbonates may be used. Nitrides such as silicon nitride, silicon nitride, and aluminum nitride may be used. Halogenides such as fluorspar may be used. Phosphates such as apatite may be used. Barium titanate, and lead zirconate-titanate may be used. Ferrite, steatite, forsterite, cordierite, sialon, zircon and the like may be used. Besides, high-temperature superconductive ceramics, machinable ceramics, and the like may be used. Fiber-reinforced ceramics using carbon fiber, organic fiber, metal fiber, glass fiber, and the like may be used. The shape thereof may be identical to that of the aforementioned base A, and may be different.

No special limit is also put to the aforementioned organic materials as well. The material having a type identical to that of the constituent materials of the aforementioned base A are employed for this organic materials. Needless to say, organic materials other than them may be used. The shape thereof may be identical to that of the aforementioned base A, and may be different.

[The Surface Treatment of the Base A (Modification Treatment: Adhesion Treatment)]

At first, the solution having aforementioned adhesiveness improver (aforementioned compound ($\alpha$): molecular adhesive) dissolved therein or the dispersion is prepared. As solvents to be employed, water, alcohols (for example, methanol, ethanol, isopropanol, ethylene glycol, propylene glycol, cellosolve and carbitol), ketones (for example, acetone, methyl ethyl ketone and cyclohexanone), aromatic hydrocarbons (for example, benzene, toluene and xylene), aliphatic hydrocarbons (for example, hexane, octane, decane, dodecane and octadecane), esters (for example, ethyl acetate, methyl propionate and methyl phthalate), ethers (for example, tetrahydrofuran, ethyl butyl ether, and anisole), and the like can be listed. Mixtures of the aforementioned compounds may be also used. The containing amount of the aforementioned compound ($\alpha$) is 0.0001 to 10% by weight. Particularly preferably, it is 0.001 to 2% by weight. The reason is that when the containing amount of the aforementioned compound ($\alpha$) is too few, its effect is scanty. To the contrary, it does not make sense that the containing amount is too much because the amount of the reaction with the base A is limited. The above-mentioned ratio was preferred from such a viewpoint.

Surfactants are added to the aforementioned solution (dispersion) according to a necessity from a viewpoint of adjusting surface tension. For example, nonionic surfactants (for example, nonionic surfactants that are comprised of long-alkyl chains and polyethylene glycol), cationic surfactants (for example, quaternary ammonium salts), or anionic surfactants (for example, organic carboxylate and sulfonate) are employed.

The base A is immersed into the aforementioned solution (dispersion). Or, the aforementioned solutions (dispersions) are sprayed onto the base A. This allows the aforementioned adhesiveness improver (the aforementioned compound ($\alpha$): molecular adhesive) to stick to the base A surface.

Thereafter, light (ultraviolet rays) is radiated. In particular, only locations in which the aforementioned compound ($\alpha$) should be bonded to the aforementioned base A are irradiated with light. For this, an appropriate pattern mask is used. With the aforementioned ultraviolet ray irradiation, the azide group of the aforementioned compound ($\alpha$) is dissolved. Dissolution of the azide group allows nitrene to be generated. This nitrene attacks the functional groups (for example, $-CH_3$, $-CH_2-$, and $-CH<$, $-CH=CH-$) existing on the aforementioned base A surface. And, a hydrogen-abstraction radical addition reaction or a radical addition reaction occurs, and the chemical bonding between the aforementioned compound ($\alpha$) and the base A surface is yielded. No chemical bonding occurs in the not-irradiated locations.

UV devices (for example, high-pressure mercury UV lamps, low-pressure mercury UV lamps, fluorescence type UV lamps (short ARC xenon lamps and chemical lamps) and metal halide lamps) are employed for the ultraviolet ray irradiation. And the ultraviolet rays having a wavelength of 200 to 450 nm are radiated. When the light intensity of irradiation is too few, the reaction hardly progresses. To the contrary, when the light intensity of irradiation is too much, there is an anxiety over deterioration in the base A. Thus, the preferable light intensity of irradiation (wavelength 254 nm) is $1\ mJ/m^2$ to $5\ J/m^2$. More preferably, it is $5\ mJ/m^2$ to $1\ J/m^2$.

When the base A is complicatedly shaped, so as to uniformly irradiating the base A with UV, use of reflection plates is effective. As the reflection plates, for example, mirrors, surface-polished metal foil, Al mirror surface foil, SUS mirror surface foil and silver plating mirror surface plates can be listed. Shape, size and materials of the reflection plate, and the like are appropriately selected from a viewpoint of reflection efficiency.

The aforementioned base A subjected to the ultraviolet ray irradiation is treated with water. For example, it is immersed into water. Water is preferably an acid aqueous solution or an alkaline aqueous solution. For example, the base A is immersed into a 0.0001% to 10% (preferably, 0.01% to 5%) acid aqueous solution for 0.1 to 60 minutes (preferably, 1 to 20 minutes). This allows the alkoxysilyl group to be modified into the hydroxylsilyl group. The aforementioned conditions of the numerical value are decided from a viewpoint of efficiency of the modification of the alkoxysilyl group into the hydroxylsilyl group.

The polymer having the aforementioned general formula [II] is preferably used together with the aforementioned compound ($\alpha$). That is, using the polymer having the aforementioned general formula [II] together with the aforementioned compound ($\alpha$) causes the number of $-OH$ existing on the base A surface to be increased. That is, the polymer containing the alkoxy group having the aforementioned general formula [II] is employed, thereby causing the number of $-OH$ existing on the base A surface to be increased.

The treatment by the aforementioned polymer containing the alkoxy group is performed similarly to the treatment by the aforementioned compound ($\alpha$). That is, the base A is treated with the solution or dispersion containing the polymer having the aforementioned general formula [II]. As the solvents to be employed for the aforementioned treatment, water, alcohols (for example, methanol, ethanol, isopropanol, ethylene glycol, propylene glycol, cellosolve and carbitol), ketones (for example, acetone, methyl ethyl ketone and cyclohexane), aromatic hydrocarbons (for example, benzene, toluene and xylene), aliphatic hydrocarbons (for example, hexane, octane, decane, dodecane and octadecane), esters (for example, ethyl acetate, methyl propionate and methyl phthalate), ethers (for example, tetrahydrofuran, ethyl butyl ether, and anisole), and the like can be listed. Mixtures of the aforementioned compounds group may be also used. The containing amount of the aforementioned polymer containing the alkoxy group is 0.0001 to 10% by weight. Particularly preferably, it is 0.001 to 5% by weight. The reason is that when the containing amount of the aforementioned polymer is too few, its effect is scanty. After the treatment by the aforementioned polymer, the base A is subjected to heat treatment at a temperature of 0 to 200° C. (preferably, 20 to 150° C.) and for 0.1 to 60 minutes (preferably, 1 to 20 minutes).

Further, the treatment by the compounds represented by the aforementioned general formulas [T], [III] or [IV] is also preferable in addition to the use of the aforementioned compound (α). That is, using the compounds represented by the aforementioned general formulas [T], [III] or [IV] together with the aforementioned compound (α) causes the number of —OH existing on the base A surface to be increased. That is, employment of the compounds represented by the aforementioned general formulas [T], [III] or [IV] causes the number of —OH existing on the base A surface to be increased. In addition, reactive functional groups are introduced.

The treatment by the compounds represented by the aforementioned general formulas [T], [III] or [IV] is performed similarly to the treatment by the aforementioned compound (α). That is, the base A is treated with the solution or the dispersion containing the compounds represented by the aforementioned general formulas [T], [III] or [IV]. As the solvents to be employed for the aforementioned treatment, water, alcohols (for example, methanol, ethanol, isopropanol, ethylene glycol, propylene glycol, cellosolve and carbitol), ketones (for example, acetone, methyl ethyl ketone and cyclohexane), aromatic hydrocarbons (for example, benzene, toluene and xylene), aliphatic hydrocarbons (for example, hexane, octane, decane, dodecane and octadecane), esters (for example, ethyl acetate, methyl propionate and methyl phthalate), ethers (for example, tetrahydrofuran, ethyl butyl ether, and anisole), and the like can be listed. Mixtures of the aforementioned compounds may be also used. The containing amount of the aforementioned compound is 0.0001 to 10% by weight. Particularly preferably, it is 0.001 to 5% by weight. The reason is that when the containing amount of the aforementioned compound is too few, its effect is scanty. After the treatment by the aforementioned compounds, the base A is subjected to heat treatment at a temperature of 0 to 200° C. (preferably, 20 to 150° C.) and for 0.1 to 60 minutes (preferably, 1 to 20 minutes).

The present invention makes it possible to employ the compounds (coupling agents containing the alkoxysilyl group) represented by the aforementioned general formulas [T], [III] or [IV]. With this, various functional groups are introduced into the base A surface. As the coupling agents of this type, for example, 6-alkoxysilylpropylamino-1,3,5-triazine-2,4-dithiol monosodium, 6-bis(3-alkoxysilylpropyl)amino-1,3,5-triazine-2,4-dithiol monosodium, 6-N-cyclohexyl-N-(3-(triethoxysilyl)propylamino)-1,3,5-triazine-2,4-dithiol monosodium, vinylmethoxy siloxane homopolymer, bis(triethoxysilylpropyl)tetrasulfide, 3-mercaptopropyl trimethoxysilane, 3-aminopropyl triethoxysilane, 6-alkoxysilyl propylamino-1,3,5-triazine-2,4-dithiol, 3-alkoxysilylpropyl amine, bis(3-alkoxysilylpropyl)amine, 6-N-cyclohexyl-N-3-(triethoxysilyl)propylamine, 3-aminopropyl triethoxysilane, (3-acryloxypropyl)trimethoxysilane, methacryloxypropyl trimethoxysilane, triethoxysilyl undecanal, 4-aminobutyl triethoxysilane, m-aminophenyl triethoxysilane, 11-aminoundecyl trimethoxysilane, N-(3-triethoxysilylpropyl)pyrrole, N-(2-aminoethyl)-3-aminopropyl trimethoxysilane, 3-aminopropylmethyl diethoxysilane, aminopropylsilanetriol, N-(2-aminoethyl)-3-aminopropylsilanetriol, N-methylaminopropyl trimethoxysilane, N-butylaminopropyl trimethoxysilane, N-trimethoxysilylpropyl trimethyl ammonium chloride, bis(trimethoxysilylpropyl)amine, 3-(triethoxysilyl)propyl succinic anhydride, 6-azide sulfonylhexyl triethoxysilane, 2-(4-chlorosulfonyl)ethyltriethoxysilane, 2-(3,4-epoxycyclohexyl)trimethoxysilane, (3-glycidioxypropyl)trimethoxysilane, 10-(carbomethoxy) decyl dimethyl methoxysilane, 3-chloropropyl trimethoxysilane, 7-bromoheptyl trimethoxysilane, 3-isocyanatopropyl triethoxysilane, (3-triethoxysilyl)-t-butylcarbamate, 2-(diphenylphosphino)ethyl triethoxysilane, diethylphosphate ethyltriethoxysilane, 3-mercaptopropyl trimethoxysilane, 5-(bicycloheptinyl)triethoxysilane, (3-cyclopentadiene-1ylpropyl)triethoxysilane, and the like can be listed.

The treatment by these coupling agents is also performed similarly to the treatment by the aforementioned compound (α) and the treatment by the aforementioned polymer containing the alkoxy group. As the solvents to be employed, for example, water, alcohols (for example, methanol, ethanol, isopropanol, ethylene glycol, propylene glycol, cellosolve and carbitol), ketones (for example, acetone, methyl ethyl ketone and cyclohexane), aromatic hydrocarbons (for example, benzene, toluene and xylene), aliphatic hydrocarbons (for example, hexane, octane, decane, dodecane and octadecane), esters (for example, ethyl acetates, methyl propionate and methyl phthalate), ethers (for example, tetrahydrofuran, ethyl butyl ether, and anisole), and the like can be listed. The containing amount of the aforementioned coupling agents is 0.0001 to 10% by weight. Particularly preferably, it is 0.001 to 5% by weight. The reason is that when the containing amount of the aforementioned coupling agents is too few, its effect is scanty. After the treatment by the aforementioned coupling agents the base is subjected to heat treatment at a temperature of 0 to 200° C. (preferably, 20 to 150° C.) and for 0.1 to 60 minutes (preferably, 1 to 20 minutes).

[The Surface Treatment of the Base B (Modification Treatment: Adhesion Treatment)]

The materials of the base B, as described previously, are metals, ceramics, or organic materials.

Metals or ceramics basically include the OH group. Thus, the adhesion by the chemical bonding between the base B of this type and the base A subjected to the aforementioned surface treatments is possible even though a special surface treatment is not performed. However, there is also the case in which the surface of the base B has been contaminated. In this case, it becomes necessary to make the surface clean. For example, the cleaning treatment by the cleaning agent, the ultraviolet ray irradiation treatment, the corona discharge treatment or the plasma treatment is performed.

As described previously, a special treatment is unnecessary in the case of metals and ceramics. However, the treatment by the compounds represented by the aforementioned general formulas [II], [T], [III] and [IV] may be performed.

A treatment similar to the treatment performed for the base A is preferably performed for the base B made of the organic materials.

[Bonding (Adhesion) Between the Base A and the Base B]

There are fluid adhesion and non-fluid adhesion for a type of adhesion. In the fluid adhesion, an adhesive flows in an adhesion stage, and the adhesive and an adhered contact each other. In the non-fluid adhesion, the adhesive deforms within an elastic deformation range in the adhesion stage, and the adhesive and the adhered contact each other. In any case, there are case of liquidity and the case of illiquidity for the adhered.

In the adhesion between the aforementioned base A and the aforementioned base B, the following combinations are thinkable, dependent upon which is used as the adhesive.

(1) The fluid adhesion in the case in which the base A is the adhesive (fluid) and the base B is the adhered (non-fluid such as metals and ceramics)

(2) The fluid adhesion in the case in which the base B is the adhesive (organic materials: fluid) and the base A is the adhered (the adhesion temperature is equal to or less than a glass transit temperature (Tg))

(3) The non-fluid adhesion in the case in which the base A is the adhesive (non-fluid) and the base B is the adhered (non-fluid such as metals and ceramics)

(4) The non-fluid adhesion in the case in which the base B is the adhesive (organic materials: non-fluid) and the base A is the adhered (the adhesion temperature is equal to or less than a glass transit temperature (Tg))

With the case of the aforementioned (1), the base A (the adhesive with fluidity) is curing resin (thermosetting resin and photo-curing resin) not subjected to curing, thermoplastic resin, vulcanized rubber not subjected to crosslinking, or a coating film not subjected to curing applied onto the surface.

With the case of the aforementioned (2) in which the adhesion temperature is a glass transit temperature Tg to a melting point Tm of the material, the base B with fluidity is curing resin (thermosetting resin and photo-curing resin) not subjected to curing, thermoplastic resin, vulcanized rubber not subjected to crosslinking, or a coating film not subjected to curing applied onto the surface.

In the fluid adhesion, the adhesive with fluidity is caused to contact the adhered with non-fluidity at a temperature of 0 to 400° C. (preferably, 20 to 250° C.) and for 0.1 second to 200 minutes (preferably, 1 second to 100 minutes) under pressurization of 0.01 to 50 MPa (preferably, 0.1 to 5 MPa) (or under decompression of 0.0099 to 0.00001 Pa (preferably, 0.009 to 0.0001 Pa)). A vacuum dryer, a vacuum packing machine, a pressing machine, an extruder, an injection molding machine, a roll, or the like is employed in this treatment. With this, an adhesion complex of the base A and the base B was obtained. There was a possibility that the adhesion (chemical reaction: chemical bonding) was insufficient existed when the above conditions were not met.

With the case of the aforementioned (3) in which the base A with non-fluidity is the adhesive and the base B is the adhered (non-fluid such as metals and ceramics), the base A with non-fluidity is curing resin (thermosetting resin and photo-curing resin), thermoplastic resin, vulcanized rubber, a cured coating film, or the like.

With the case of the aforementioned (4) in which the base B with non-fluidity is the adhesive and the base A with non-fluidity is the adhesive, each of the base B with non-fluidity and the base A with non-fluidity is curing resin (thermosetting resin and photo-curing resin), thermoplastic resin, vulcanized rubber, a cured coating film, or the like.

In the non-fluid adhesion, the adhesive with non-fluidity is caused to contact the adherent with non-fluidity at a temperature of 0 to 400° C. (preferably, 20 to 250° C.), for 0.1 second to 200 minutes (preferably, 1 second to 100 minutes), and under pressurization of 0.01 to 50 MPa (preferably, 0.1 to 5 MPa) (or under decompression of 0.0099 to 0.00001 Pa (preferably, 0.009 to 0.0001 Pa)). A vacuum dryer, a vacuum packing machine, a pressing machine, an extruder, an injection molding machine, a roll, or the like is employed in this treatment. With this, an adhesion complex of the base A and the base B was obtained. Additionally, there was a possibility that the adhesion (chemical reaction: chemical bonding) was insufficient when the above conditions were not met.

Additionally, one of the criteria for determining whether the adhesion is non-fluid adhesion or fluid adhesion is whether the adhesion temperature is equal to or more than the glass transit temperature (Tg), or falls under a temperature range of Tg to Tm (melting point).

Hereinafter, the specific examples are list for explanation. However, the preset invention is not limited to the following examples.

EXAMPLE (1) A Novel Compound α(—OH Imparting Agent)

Example A-1

0.1 mol (18.4 g) of cyanuric chloride was added to 200 ml of an acetone solution at a temperature of 0 to 5° C. 100 ml of an aqueous solution containing 0.204 mol of $NaN_3$ was dripped into this cyanuric chloride solution while it was stirred. The stirring continued to be performed for 30 minutes also after the dripping was finished. Thereafter, an organic layer was extracted with ether from this mixture solution. And, filtering was performed. Thereafter, the ether was removed with a rotary evaporator. Next, a crude product was obtained with depressurized drying. The crude product was refined with a silica gel column chromatography (developing solvent: mixture solvent (chloroform: hexane=1:2)). The obtained refined product was oil-formed. The amount thereof was 18.1 g (a yield: 91.5%).

The obtained refined product (compound) was identified by an element analysis measurement device, an NMR measurement device and an MS measurement device. As a result, the refined product was determined to be 2,4-diazide-6-chloro-1,3,5-triazine (DAMC). The element analysis measurement device is Perkin Elmer model 2400CHN. The NMR measurement device is AC400P made by Bruker Japan Co. ltd. The MS measurement device is JEOL JMS-700. An element analysis measurement device, an NMR measurement device and an MS measurement device to be used hereinafter are identical to the aforementioned devices, respectively.

DAMC $^{13}C$ NMR (101 MHz, $CDCl_3$) δ 171.4, 172.6

EI-MS (70 eV) m/z 197 (M+)

Element analysis (actual value/calculated value) C: 18.3/18.24, N: 63.6/63.81

9.88 g (0.050 mol) of the aforementioned DAMC was added to 100 ml of tetrahydrofuran (THF). And, it was placed under a nitrogen environment. 100 ml of a THF solution containing 0.050 mol (11.5 ml) of 3-triethoxysilylpropyl amine and 0.051 mol (7.2 ml) of triethyl amine was dripped into this DAMC solution. And, the stirring was performed for 120 minutes at a temperature 50° C. The generated triethylamine hydrochloride was removed after the reaction was finished. THF was evaporated under depressurization (20 mmHg), and the crude product was obtained. The obtained crude product was refined by the silica gel column chromatography (developing solvent: chloroform). The obtained refined product was white powder. The amount thereof was 18.55 g (a yield: 97%).

The obtained refined product (compound) was identified by the element analysis measurement device, the NMR measurement device and the MS measurement device. As a result, the refined product was determined to be 6-(3-triethoxysilyl-propyl)amino-1,3,5-triazine-2,4-diazide (TE-DAZ).

TE-DAZ $^{1}H$ NMR (400 MHz, $CDCl_3$) δ 0.67 (t, J=8.0 Hz, 2H, CH2CH2Si), 1.23 (t, J=7.0 Hz, 9H, SiOCH2CH3), 1.73 (quint., 2H, CH2CH2CH2Si), 3.46 (q, J=8.0 Hz, 2H, NHCH2CH2), 3.83 (q, J=7.0 Hz, 6H, SiOCH2CH3), 6.36 (br s, 1H, NHCH2CH2CH2)

$^{13}C$ NMR (101 MHz, $CDCl_3$) δ 7.7, 18.2, 22.5, 43.4, 58.5, 166.8, 169.6, 170.3

EI-MS (70 eV) m/z 382 (M$^+$).

Element analysis (actual value/calculated value) C: 37.4/37.69, H: 5.9/5.80, N: 36.9/36.62

Example A-2

The synthesis was performed in accordance with the aforementioned example A-1.

That is, in the aforementioned example A-1, the synthesis was performed similarly except that 0.050 mol (21.9 ml) of bis(3-triethoxysilylpropyl)amine was employed instead of 0.050 mol (11.5 ml) of 3-triethoxysilylpropyl amine. The obtained refined product was oil-formed. The amount thereof was 28.17 g (a yield: 96%).

The obtained refined product (compound) was identified by the element analysis measurement device, the NMR measurement device and the MS measurement device. As a result, the refined product was determined to be 6-bis(3-triethoxysilylpropyl)amino-1.3.5-triazine-2,4-diazide (BTE-DAZ).

BTE-DAZ
$^1$H NMR (400 MHz, CDCl$_3$) d 0.59 (t, J=8.0 Hz, 4H, CH2CH2Si), 1.22 (t, J=6.9 Hz, 18H, SiOCH2CH3), 1.66-1.74 (m, 4H, CH2CH2CH2Si), 3.53 (t, J=8.0 Hz, 4H, NCH2CH2), 3.82 (q, J=6.9 Hz, 12H, SiOCH2CH3)
$^{13}$C NMR (101 MHz, CDCl$_3$) d 7.6, 18.3, 20.9, 50.2, 58.4, 165.3, 169.8
EI-MS (70 eV) m/z 586 (M$^+$)
Element analysis (actual value/calculated value) C: 43.2/42.98, H: 7.3/7.21, N: 23.6/23.87

Example A-3

The synthesis was performed in accordance with the aforementioned example A-1.

That is, in the aforementioned example A-1, the synthesis was performed similarly except that 0.102 mol of NaN$_3$ was employed. The obtained refined product was oil-formed. The amount thereof was 17.2 g (a yield: 90%).

The obtained refined product (compound) was identified by the element analysis measurement device, the NMR measurement device and the MS measurement device. As a result, the refined product was determined to be 2-azide-4,6-dichloro-1,3,5-triazine (MADC).

MADC
$^{13}$C NMR (101 MHz, CDCl$_3$) d 171.5, 172.8
EI-MS (70 eV) m/z 190 (M+)
Element analysis (actual value/calculated value) C: 18.5/18.87, N: 44.3/44.01

4.35 g (0.023 mol) of the aforementioned MADC was added to 50 ml of tetrahydrofuran (THF). And, it was placed under a nitrogen environment. 40 ml of the THF solution containing 0.048 mol (11 ml) of 3-aminopropyl triethoxysilane was dripped into this MADC solution. Thereafter, 40 ml of the THF solution containing 0.048 mol (6.8 ml) of triethylamine was dripped. After the dripping was finished, the temperature rising treatment was performed until the temperature of the reaction solution was raised to 45° C. Thereafter, the stirring was performed for one hour. The reaction solution was cooled down to the room temperature. The ammonium salts were deposited, whereby separation filtering was executed by means of suction filtration. The filtrate was condensed by the rotary evaporator. The crude product was obtained by means of the depressurized drying. The crude product was refined by the silica gel column chromatography (developing solvent: mixture solvent (ethyl acetate:hexane=1:2)). The obtained refined product was colorless and oil-formed. The amount thereof was 10.86 g (a yield: 85%).

The obtained refined product (compound) was identified by the element analysis measurement device, the NMR measurement device and the MS measurement device. As a result, the refined product was determined to be 2-azide-4,6-bis(3-triethoxysilylpropyl)amino-1,3,5-triazine (TE-MAZ).

TE-MAZ
$^1$H NMR (400 MHz, CDCl$_3$) d 0.66 (t, J=8.0 Hz, 4H, CH$_2$CH$_2$Si), 1.23 (t, J=7.0 Hz, 18H, SiOCH$_2$CH$_3$), 1.69 (br s, 4H, CH$_2$CH$_2$CH$_2$Si), 3.34-3.42 (m, 4H, NCH$_2$CH$_2$), 3.82 (q, J=7.0 Hz, 12H, SiOCH$_2$CH$_3$), 5.40, 5.54 and 5.64 (br s×3, 2H, NHCH$_2$) FAB-MS m/z 561 (M$^+$+1);
Element analysis (actual value/calculated value) C: 45.1/44.98, H: 8.2/7.91, N: 20.1/19.98

(2) Surface Modification by a Novel Compound α (—OH Imparting Agent)

Example 1 to 5

APP (polypropylene) plate subjected to ultrasonic cleaning (time: 10 minutes) in ethanol of which a temperature was 40° C. was employed as the base A.

This PP plate was immersed (time: 5 minutes) into an ethanol solution (temperature: 20° C.) of the aforementioned TE-DAZ (concentration: 0.01 to 0.4 wt %). After lifting up, the warm-air drying was performed. Next, a high-pressure mercury lamp (output: 2 kW, EYEMINIGRANTAGE made by EYE GRAPHICS CO. Ltd.) was employed and the ultraviolet ray irradiation of 30 mJ/cm$^2$ was performed. Thereafter, the ultrasonic cleaning was performed in the ethanol.

Comparative Example 1

The steps were taken in accordance with the example 5. That is, the steps were taken likewise except that azide sulfonate hexyl triethoxysilane (TE-ASH) was employed instead of TE-DAZ.

[Properties]

A result (presence or not of the alkoxysilyl group on the substrate surface: an XPS analysis (X-ray Photoelectron Spectroscopy: PHI-QunteraSXM made of ULVAC-PHI)) of the modification treatment by the aforementioned examples 1 to 5 and comparative example 1 is shown in Table-1.

TABLE 1

| Example | Molecular adhesive | Analysis value (at. %) | |
|---|---|---|---|
| (Comparative example) | wt. % | N1s | Si2p |
| Example 1 | TE-DAZ: 0.01 | 0.4 | 0.1 |
| Example 2 | TE-DAZ: 0.05 | 4.2 | 0.9 |
| Example 3 | TE-DAZ: 0.10 | 12.7 | 2.7 |
| Example 4 | TE-DAZ: 0.20 | 15.0 | 3.2 |
| Example 5 | TE-DAZ: 0.40 | 19.3 | 4.1 |
| Comparative example 1 | TE-ASH: 0.40 | 0 | <0.1 |

N1s indicates presence or not of the triazine ring, and Si2p indicates presence or not of the alkoxysilyl group in the Table-1. Thus, the fact that the numerical values of N1s and Si2p are confirmed indicates presence of trialkoxysilylpropylamino triazinyl group on the surface of the PP plate.

It can be seen from the result of the examples 1 to 5 that when the concentration of the TE-DAZ is higher, the trialkoxysilylpropylamino triazinyl group is more numerous.

Additionally, as apparent from the comparative example 1, when the compound containing no triazine ring is employed, the alkoxysilyl group does not exist on the surface of the PP plate even though this compound contains the azide group.

This indicates that the TE-ASH is hardly bonded to the PP surface even though the TE-ASH, being an azide compound containing no triazine ring, is employed in a state of a high concentration. That is, it was thought that a reaction activity was low even though the nitrene was generated with the ultraviolet ray irradiation, and no reaction occurred in the case of an extent in which the nitrene was absorbed on the surface of the PP plate even though the reaction occurred in a mixture state.

Examples 6 to 11

The steps were taken in accordance with the example 2. However, in these examples, a technique of blowing away an ethanol solution of the TE-DAZ (concentration: 0.1 wt %) onto the PP plate was employed instead of the technique of immersing the PP plate into an ethanol solution of the TE-DAZ.

The ultraviolet ray irradiation amount (exposure amount) is 10 to 200 mJ/cm$^2$.

Comparative Example 2

The comparative example 2 was performed in accordance with the example 11. However, in this comparative example, the TE-ASH was employed instead of the TE-DAZ.

[Properties]

A result (the XPS analysis) of the modification treatment by the aforementioned examples 6 to 11 and comparative example 2 is shown in Table-2.

TABLE 2

| | Exposure amount | Analysis value (at. %) | |
|---|---|---|---|
| | (mJ/cm$^2$) | N1s | Si2p |
| Example 6 | 10 | 8.5 | 1.8 |
| Example 7 | 20 | 12.7 | 2.7 |
| Example 8 | 30 | 14.1 | 3.0 |
| Example 9 | 50 | 16.0 | 3.4 |
| Example 10 | 100 | 17.4 | 3.7 |
| Example 11 | 200 | 17.9 | 3.8 |
| Comparative example 2 | 200 | 0 | <0.1 |

It can be seen from Table-2 that when the ultraviolet ray irradiation amount is much, the trialkoxysilylpropylamino triazinyl group and the triazinylidene group bonded to the surface of the PP plate are more numerous.

Additionally, as a rule, the exposure amount to be used for the photoreaction such as photo-curing is 200 mJ/cm$^2$ or more.

However, it can be seen that the chemical reaction with the resin plate occurred even though the ultraviolet ray irradiation amount is few in these examples. By the way, it was confirmed that the chemical reaction occurred between the TE-DAZ and the resin plate even with a low amount of the irradiation, 1 mJ/cm$^2$ or something like it.

With the case of the TE-ASH, the chemical reaction amount is few even though the ultraviolet ray irradiation amount is much.

Examples 12 to 14

The steps were taken in accordance with the example 1. However, in these examples, the concentration of the TE-DAZ is 0.5 wt % or less, and yet the ultraviolet ray irradiation amount (exposure amount) is 10 to 200 mJ/cm$^2$.

Comparative Examples 3 to 5

The comparative examples 3 to 5 were performed in accordance with the examples 12 to 14. However, in these comparative examples, the TE-ASH was employed instead of the TE-DAZ.

[Properties]

A result (the XPS analysis) of the modification treatment by the aforementioned examples 12 to 14 and comparative examples 3 to 5 is shown in Table-3.

TABLE 3

| | Exposure amount | Si2p (at. %) | | | | | |
|---|---|---|---|---|---|---|---|
| | (mJ/cm$^2$) | 0 | 0.1 | 0.2 | 0.3 | 0.4 | 0.5 |
| | | TE-DAZ concentration (wt. %) | | | | | |
| Example 12 | 10 | 0 | 1.8 | 2.3 | 2.6 | 2.8 | 2.8 |
| Example 13 | 50 | 0 | 3.2 | 3.7 | 4.0 | 4.0 | 4.0 |
| Example 14 | 200 | 0 | 3.9 | 4.0 | 4.0 | 4.1 | 4.2 |
| | | TE-ASH concentration (wt. %) | | | | | |
| Comparative example 3 | 10 | 0 | 0 | 0 | 0 | 0 | 0 |
| Comparative example 4 | 50 | 0 | 0 | 0 | 0 | 0 | 0 |
| Comparative example 5 | 200 | 0 | 0 | 0 | 0 | 0 | 0 |

It can be seen from Table-3 that when the ultraviolet ray irradiation amount is much, and yet the concentration of the TE-DAZ is higher, the trialkoxysilylpropylamino triazinyl group and the triazinylidene group bonded to the surface of the PP plate are more numerous.

Examples 15 to 26

The steps were taken in accordance with the example 6. However, in these examples, a LD-PE (low-density polyethylene) plate, the PP plate, a PA-6 (6-nylon) plate, and an EP (epoxy resin) plate were employed as the base A. A ultrasonic cleaning similar to that of the example 1 was also performed for these plates. Further, the aforementioned BTE-DAZ, and the aforementioned TE-MAZ, and the like were also employed instead of the TE-DAZ. The concentration of the TE-DAZ, the BTE-DAZ, and the TE-MAZ in the used solution was 0.1 wt %, respectively, and the ultraviolet ray irradiation amount was 30 mJ/cm$^2$, respectively.

Comparative Examples 6 to 9

The comparative examples 6, 7, 8, and 9 were performed in accordance with the examples 15, 18, 21, and 24. However, in these comparative examples, the TE-ASH was employed instead of the TE-DAZ.

[Properties]

A result (the XPS analysis) of the modification treatment by the aforementioned examples 15 to 26 and comparative examples 6 to 9 is shown in Table-4.

TABLE 4

| | | Molecular | Analysis value (at. %) | |
|---|---|---|---|---|
| | Resin | adhesive | N1s | Si2p |
| Example 15 (Comparative example 6) | LD-PE | TE-DAZ | 15.4 (<0.1) | 3.6 (<0.1) |
| Example 16 | LD-PE | BTE-DAZ | 14.9 | 7.8 |
| Example 17 | LD-PE | TE-MAZ | 14.2 | 6.9 |

TABLE 4-continued

| | Resin | Molecular adhesive | Analysis value (at. %) | |
|---|---|---|---|---|
| | | | N1s | Si2p |
| Example 18 (Comparative example 7) | PP | TE-DAZ | 13.5 (<0.1) | 2.9 (<0.1) |
| Example 19 | PP | BTE-DAZ | 13.8 | 5.6 |
| Example 20 | PP | TE-MAZ | 15.8 | 4.0 |
| Example 21 (Comparative example 8) | PA-6 | TE-DAZ | 20.4 (12.5) | 3.8 (<0.1) |
| Example 22 | PA-6 | BTE-DAZ | 19.2 | 4.8 |
| Example 23 | PA-6 | TE-MAZ | 18.6 | 4.3 |
| Example 24 (Comparative example 9) | EP | TE-DAZ | 16.0 (9.8) | 3.3 (<0.1) |
| Example 25 | EP | BTE-DAZ | 14.2 | 4.5 |
| Example 26 | EP | TE-MAZ | 13.6 | 2.3 |

Examples 27 to 44

The steps were taken in accordance with the example 15. However, in these examples, an HD-PE (high-density polyethylene) plate, a PVC (polyvinyl chloride) plate, an EP plate, a PSt (polystyrene) plate, an ABS plate, a PET (polyester) plate, a PMMA (polymethyl methacrylate) plate, a PC (polycarbonate) plate, a POM (polyacetal) plate, a PBT (polybutylene terephthalate) plate, a PU (polyurethane) plate, a USPE (unsaturated polyester) plate, a PPE (polyphenylene ester) plate, a PI (polyimide) plate, a PPS (polyphenylene sulfide) plate, a PEEK (polyether keton) plate, a LCP (liquid crystal polymer) plate, and a PTEE (polytetrafluoroethylene) plate were employed as the base A.

Comparative Examples 10 to 15

The comparative example 10, the comparative example 11, the comparative example 12, the comparative example 13, the comparative example 14, and the comparative example 15 were performed in accordance with the example 27, the example 30, the example 32, the example 34, the example 39, and the example 43, respectively. However, in these comparative examples, the TE-ASH was employed instead of the TE-DAZ.

[Properties]
A result (the XPS analysis) of the modification treatment by the aforementioned examples 27 to 44 and comparative examples 10 to 15 is shown in Table-5.

TABLE 5

| Example | High polymerized material | Analysis value (at. %) | |
|---|---|---|---|
| | | N1s | Si2p |
| Example 27 (Comparative example 10) | HD-PE | 14.4 (0) | 3.2 (<0.1) |
| Example 28 | PVC | 9.8 | 6.2 |
| Example 29 | EP | 16.9 | 3.3 |
| Example 30 (Comparative example 11) | PSt | 10.2 (0) | 2.2 (<0.1) |
| Example 31 | ABS | 5.7 | 0.3 |
| Example 32 (Comparative example 12) | PET | 14.1 (0) | 2.9 (0.2) |
| Example 33 | PMMA | 3.2 | 0.8 |
| Example 34 (Comparative example 13) | PC | 16.2 (0) | 3.4 (<0.1) |
| Example 35 | POM | 8.9 | 2.5 |
| Example 36 | PBT | 16.2 | 3.4 |
| Example 37 | Urethane resin | 20.2 | 3.2 |
| Example 38 | Unsaturated polyester | 11.2 | 2.6 |
| Example 39 (Comparative example 14) | PPE | 16.2 (0) | 3.4 (<0.1) |
| Example 40 | PI | 21.6 | 4.8 |
| Example 41 | PPS | 16.7 | 3.3 |
| Example 42 | PEEK | 3.8 | 0.8 |
| Example 43 (Comparative example 15) | LCP | 12.6 (0) | 3.1 (<0.1) |
| Example 44 | PTFE | 18.7 | 3.9 |

Examples 45 to 53

The steps were taken in accordance with the example 15. However, in these examples, a NR (natural rubber) plate, a IR (isoprene rubber) plate, a BR (butadiene rubber) plate, a NBR (nitrile butadiene rubber) plate, a SBR (styrene butadiene rubber) plate, a FKM (flourine rubber) plate, a SBS (styrene butadiene styrene-block copolymer) plate, a Q (silicone rubber) plate, and a EPDM (ethylene propylene diene rubber) plate were employed as the base A.

Comparative Examples 16 to 18

The comparative example 16, the comparative example 17, and the comparative example 18 were performed in accordance with the example 48, the example 50, and the example 53, respectively. However, in these comparative examples, the TE-ASH was employed instead of the TE-DAZ.

[Properties]
A result (the XPS analysis) of the modification treatment by the aforementioned examples 45 to 53 and comparative examples 16 to 18 is shown in Table-6.

TABLE 6

| Example | High polymerized material | Analysis value (at. %) | |
|---|---|---|---|
| | | N1s | Si2p |
| Example 45 | NR | 1.1 | 0.8 |
| Example 46 | IR | 5.3 | 1.3 |
| Example 47 | BR | 8.8 | 2.3 |
| Example 48 (Comparative example 16) | NBR | 9.4 (6.8) | 1.9 (<0.1) |
| Example 49 | SBR | 9.8 | 2.9 |
| Example 50 (Comparative example 17) | FKM | 3.3 (6.8) | 0.7 (<0.1) |
| Example 51 | SBS | 10.6 | 2.8 |
| Example 52 | Q | 5.7 | 1.5 |
| Example 53 (Comparative example 18) | EPDM | 7.3 (6.8) | 1.9 (<0.1) |

It can be seen from Table-4, Table-5, and table-6 that the compounds of the present invention exhibit a modification effect without depending on kinds of the resin.

Examples 54 to 59

The steps were taken in accordance with the example 1. However, in these examples, the NBR plate and the PP plate were employed as the base A.

In the example 54 and the example 57, after the ultraviolet ray irradiation and the ultrasonic cleaning in the example 1, in addition, the immersion in a solution of 0.5 wt % PDES (polydiethoxysiloxane), and the heating treatment (at a temperature of 80° C. and for ten minutes) were performed.

In the example 55 and the example 58, the steps were taken likewise except that a solution of 0.1 wt % TES (6-(3-triethoxysilylpropyl)amino-1,3,5-triazine-2,4-dithiol) was employed instead of the PDES in the example 54 and the example 57. However, the concentration of the TE-DAZ is 0.1 wt %. The heating temperature was 120° C.

In the example 56 and the example 59, the steps were taken likewise except that after the immersion into a solution of the PDES in the example 54 and the example 57, in addition, the immersion into a solution of 0.1 wt % TES was performed. However, the heating temperature was 120° C.

[Properties]

A result (the XPS analysis) of the modification treatment by the aforementioned examples 54 to 59 is shown in Table-7.

TABLE 7

| | Resin | Pre-treatment step | Post-treatment step | Analysis value (at. %) | | |
|---|---|---|---|---|---|---|
| | | | | N1s | Si2p | S2p |
| Example 54 | NBR | 0.01 wt. %-TE-DAZ | 0.5 wt. % PDES 80° C. × 10 min | 3.2 | 3.8 | — |
| Example 55 | NBR | 0.1 wt. %-TE-DAZ | 0.1 wt. % TES 120° C. × 10 min | 12.9 | 3.7 | 1.7 |
| Example 56 | NBR | 0.01 wt. %-TE-DAZ | 0.5 wt. % PDES + 0.1 wt. % TES 120° C. × 10 min | 13.2 | 5.2 | 6.9 |
| Example 57 | PP | 0.01 wt. %-TE-DAZ | 0.5 wt. % PDES 80° C. × 10 min | 2.3 | 4.8 | — |
| Example 58 | PP | 0.1 wt. %-TE-DAZ | 0.1 wt. % TES 120° C. × 10 min | 12.2 | 4.2 | 1.8 |
| Example 59 | PP | 0.01%-TE-DAZ | 0.5 wt. % PDES + 0.1 wt. % TES 120° C. × 10 min | 12.6 | 6.8 | 3.2 |

Characteristics of the modification treatment by the PDES and the TES (the bonding reaction of the PDES and the bonding reaction of the TES) can be grasped from Table-7 in addition to the characteristics of the modification treatment by the TE-DAZ.

(3) Bonding (Adhesion: Molecular Adhesion) by a Novel Compound α (—OH Imparting Agent)

Examples 61 to 72

A sheet of non-cured epoxy resin was employed as the base A.

This sheet of non-cured epoxy resin was obtained in a manner described next. 52 parts by weight of Epicoat 828 (bisphenol A-type epoxy resin made by Mitsubishi Chemical Corporation), 14 parts by weight of Epicoat 1001 (bisphenol A-type epoxy resin made by Mitsubishi Chemical Corporation), and 34 parts by weight of polyamide amine (curing agent), and 20 parts by weight of clay (filler) were kneaded with a Banbury mixer. And, a sheet having a thickness of 1 mm was obtained with a small-size two-roll machine.

An ethanol solution of 0.05 wt % TE-DAZ was blown away onto the aforementioned sheet. Thereafter, the ultraviolet ray irradiation (25 mJ/cm²) was performed.

An Al plate, a SUS 304 plate, a Glass (G) plate, and an Alumina ($Al_2O_3$) plate were prepared as the base B. Ethanol cleaning was performed for these metal plates and ceramic plates after surface polishing.

Further, the base B obtained by performing the next surface treatment for the abovementioned metal plates and ceramic plates was also prepared. That is, the abovementioned metal plates and ceramic plates were immersed into an ethanol solution of 0.1 wt % vinylmethoxy siloxane polymer (VMS).

After lifting up, the drying and the heat treatment (at a temperature of 80° C. and for ten minutes) were performed. The corona discharge treatment was performed. And, the polydiethoxysiloxane (PDES) was employed instead of the aforementioned VMS, and the steps were taken likewise except for the corona discharge treatment.

The aforementioned base A and base B were arranged in such a manner that the surfaces of the modification treatment by the TE-DAZ faced each other. And, the press force of 1 MPa was applied. The temperature at this time is 80° C., and the time is ten minutes.

Comparative Examples 61 to 72

The steps were taken in accordance with the examples 61 to 72 except that the TE-ASH was employed instead of the TE-DAZ in the examples 61 to 72.

[Properties]

In the examples 61 to 72 and the comparative examples 62 to 72, the adhesive (peeling) strength was investigated. That is, a subject was notched at a width of 10 mm. And, the adhesive strength was measured in accordance with JIS K6584-1. Shimadzu Autograph AGS (made by Shimadzu Corporation) was employed for the measurement. The measurement of the adhesive strength subsequent hereto was performed similarly to this. Further, a coverage ratio was investigated.

A result thereof is shown in Table-8.

TABLE 8

| | Modified high polymerized materials (base A) | Various types of materials (base B) | Adhesiveness | |
|---|---|---|---|---|
| | | | Adhesive strength (kN/m) | Coverage ratio (%) |
| Example 61 (Comparative example 61) | Sheet of non-cured epoxy resin | Al | 2.2 (0.5) | 100 (30) |
| Example 62 (Comparative example 62) | Sheet of non-cured epoxy resin | SUS | 2.1 (0.3) | 100 (20) |
| Example 63 (Comparative example 63) | Sheet of non-cured epoxy resin | G | 2.5 (0.1) | 100 (40) |
| Example 64 (Comparative example 64) | Sheet of non-cured epoxy resin | $Al_2O_3$ | 2.3 (0.1) | 100 (30) |
| Example 65 (Comparative example 65) | Sheet of non-cured epoxy resin | Al modified with VMS | 2.8 (0.1) | 100 (20) |
| Example 66 (Comparative example 66) | Sheet of non-cured epoxy resin | SUS modified with VMS | 2.6 (0.2) | 100 (10) |
| Example 67 (Comparative example 67) | Sheet of non-cured epoxy resin | G modified with VMS | 2.9 (0.1) | 100 (10) |
| Example 68 | Sheet of | $Al_2O_3$ modified | 3.1 (0.4) | 100 (20) |

TABLE 8-continued

| | Modified high polymerized materials (base A) | Various types of materials (base B) | Adhesiveness | |
|---|---|---|---|---|
| | | | Adhesive strength (kN/m) | Coverage ratio (%) |
| (Comparative example 68) | non-cured epoxy resin | with VMS | | |
| Example 69 (Comparative example 69) | Sheet of non-cured epoxy resin | Al modified with PDES | 2.5 (0.1) | 100 (20) |
| Example 70 (Comparative example 70) | Sheet of non-cured epoxy resin | SUS modified with PDES | 2.8 (0.2) | 100 (20) |
| Example 71 (Comparative example 71) | Sheet of non-cured epoxy resin | G modified with PDES | 2.9 (0.1) | 100 (20) |
| Example 72 (Comparative example 72) | Sheet of non-cured epoxy resin | $Al_2O_3$ modified with PDES | 2.5 (0.4) | 100 (20) |

Examples 73 to 83

A sheet of non-cured flexible polyethylene and a sheet of non-cured photo-curable epoxyacrylate were employed as the base A.

The aforementioned sheet of non-cured flexible polyethylene was obtained in a manner described next. 100 parts by weight of EXCELLEN GMH (flexible polyethylene made by Sumitomo Chemical Co. Ltd.) and 3 parts by weight of dicumyl peroxide were employed to produce a sheet of un-crosslinked non-flexible polyethylene having a thickness of 1 mm with a two-roll machine. This sheet of un-crosslinked non-flexible polyethylene was subjected to the press force of 2 MPa with a vacuum heat pressure device for 30 minutes at a temperature of 160° C.

The aforementioned sheet of non-cured flexible polyethylene was immersed into an ethanol solution of 0.1 wt % TE-DAZ. Thereafter, the ultraviolet ray irradiation (35 mJ/cm$^2$) was performed.

The aforementioned sheet of non-cured photo-curable epoxyacrylate was obtained in a manner described next. A mixture of 187 g of epoxy resin (Epicoat 828, epoxy equivalent 187) and 172 g of methacrylic acid was heated for 12 hours at a temperature of 70° C. under a nitrogen environment. 136.2 g of pentaerythritoltetrakis(3-mercaptobutyrate) (Karenz MT-PEI made by SHOWA DENKO K.K.) and 70 g of ethyl polymer acrylate (made by KANTO CHEMICAL CO., INC.) were mixed into the obtained epoxydiacrylate in the Banbury mixer. And, the coating on a PET film was performed with a coater, and a sheet having a thickness of approximate 0.1 mm was obtained.

This sheet of non-cured photo-curable epoxyacrylate was immersed into an ethanol solution of 0.1 wt % TE-DAZ. After the drying, the ultraviolet ray irradiation (35 mJ/cm$^2$) was performed.

The Al plate, the SUS 304 plate, and the Alumina ($Al_2O_3$) plate were prepared as the base B. Ethanol cleaning was performed for these metal plates and ceramic plates after surface polishing.

Further, the base B obtained by performing the next surface treatment for the abovementioned metal plates and ceramic plates was also prepared. That is, the abovementioned metal plates and ceramic plates were immersed into an ethanol solution of 0.1 wt % VMS. After lifting up, the drying and the heat treatment (at a temperature of 80° C. and for ten minutes) were performed. The corona discharge treatment was performed. Further, the PDES was employed instead of aforementioned VMS, and the steps were taken likewise except for the corona discharge treatment.

The aforementioned base A and base B were arranged in such a manner that the surfaces of the modification treatment by the TE-DAZ faced each other. And, the press force of 1 MPa was applied. The temperature at this time is 80 r, and the time is ten minutes.

Comparative Examples 73 to 83

The steps were taken in accordance with the examples 73 to 83 except that the TE-ASH was employed instead of the TE-DAZ in the examples 73 to 83.

[Properties]
In the examples 73 to 83 and the comparative examples 73 to 83, the adhesive strength and the coverage ratio were investigated.

A result thereof is shown in Table-9.

TABLE 9

| | High polymerized materials (base A) | Various types of materials (base B) | Adhesiveness | |
|---|---|---|---|---|
| | | | Adhesive strength (kN/m) | Coverage ratio (%) |
| Example 73 (Comparative example 73) | Sheet of non-cured flexible PE resine | SUS304 | 3.1 (0) | 100 (0) |
| Example 74 (Comparative example 74) | Sheet of non-cured flexible PE resine | $Al_2O_3$ | 2.9 (0) | 100 (0) |
| Example 75 (Comparative example 75) | Sheet of non-cured flexible PE resine | SUS modified with VMS | 3.5 (0) | 100 (0) |
| Example 76 (Comparative example 76) | Sheet of non-cured flexible PE resine | $Al_2O_3$ modified with VMS | 3.6 (0) | 100 (0) |
| Example 77 (Comparative example 77) | Sheet of non-cured flexible PE resine | Al | 3.1 (0) | 100 (0) |
| Example 78 (Comparative example 78) | Sheet of non-cured flexible PE resine | Al modified with PDES | 3.1 (0) | 100 (0) |
| Example 79 (Comparative example 79) | Sheet of non-cured flexible PE resine | $Al_2O_3$ modified with PDES | 3.1 (0) | 100 (0) |

TABLE 9-continued

|  | High polymerized materials (base A) | Various types of materials (base B) | Adhesiveness Adhesive strength (kN/m) | Coverage ratio (%) |
|---|---|---|---|---|
| Example 80 (Comparative example 80) | Sheet of non-cured photo-curable epoxyacrylate | SUS304 | 1.1 (0) | 100 (0) |
| Example 81 (Comparative example 81) | Sheet of non-cured photo-curable epoxyacrylate | $Al_2O_3$ | 1.0 (0) | 100 (0) |
| Example 82 (Comparative example 82) | Sheet of non-cured photo-curable epoxyacrylate | SUS modified with VMS | 1.2 (0) | 100 (0) |
| Example 83 (Comparative example 83) | Sheet of non-cured photo-curable epoxyacrylate | $Al_2O_3$ modified with VMS | 1.2 (0) | 100 (0) |

Examples 84 to 89

A sheet of epoxy resin was employed as the base A. This sheet of epoxy resin is glass epoxy resin (FR-4 made by Hitachi Chemical Co., Ltd.).

The aforementioned sheet of epoxy resin was immersed into an ethanol solution of 0.1 wt % TE-DAZ. Thereafter, the ultraviolet ray irradiation (40 mJ/cm$^2$) was performed. In addition, the aforementioned sheet of epoxy resin was immersed into an ethanol solution of 0.1 wt % TES. Thereafter, the heat treatment was performed at a temperature of 120° C. and for ten minute.

The BR plate, the SBR plate, the NBR plate, the EPR plate, the FKM plate, and the Q plate were prepared as the base B.

The aforementioned base A and base B were arranged in such a manner that the surfaces of the modification treatment by the TE-DAZ faced each other. And, the press force of 2 MPa was applied. The temperature at this time is 160° C., and the time is 30 minutes.

Comparative Examples 84 to 89

The steps were taken in accordance with the examples 84 to 89 except that the TE-ASH was employed instead of the TE-DAZ in the examples 84 to 89.

[Properties]

In the examples 84 to 89 and the comparative examples 84 to 89, the adhesive strength and the coverage ratio were investigated.

A result thereof is shown in Table-10.

TABLE 10

|  | High polymerized materials (base A) | | Various types of materials (base B) | Adhesiveness | |
|---|---|---|---|---|---|
|  | Modified resin | Functional group | | Adhesive strength (kN/m) | Coverage ratio (%) |
| Example 84 (Comparative example 84) | Modified epoxy resin | SH | BR | 4.6 (0.2) | 100 (<10) |
| Example 85 (Comparative example 85) | Modified epoxy resin | SH | SBR | 5.2 (0.4) | 100 (<10) |
| Example 86 (Comparative example 86) | Modified epoxy resin | SH | NBR | 5.7 (0.3) | 100 (<10) |
| Example 87 (Comparative example 87) | Modified epoxy resin | SH | EPR | 4.6 (0.3) | 100 (<10) |
| Example 88 (Comparative example 88) | Modified epoxy resin | SH | FKM | 4.6 (0.1) | 100 (<10) |
| Example 89 (Comparative example 89) | Modified epoxy resin | SH | Q | 3.2 (0.2) | 100 (<10) |

Examples 90 to 100

A sheet of crosslinked polyethylene was employed as the base A.

An ethanol solution of 0.05 wt % TE-DAZ was blown away onto this sheet of crosslinked polyethylene. Thereafter, the ultraviolet ray irradiation (30 mJ/cm$^2$) was performed.

The PP plate, the EP plate, the PSt plate, the PET plate, the PC plate, the POM plate, the PBT plate, the PPE plate, the PI plate, the PPS plate, and the LCP plate were prepared as the base B. The base B was also subjected to the treatment similar to that of a sheet of crosslinked polyethylene.

The aforementioned base A and base B were arranged in such a manner that the surfaces of the modification treatment by the TE-DAZ faced each other. And, the press force of 2 MPa was applied. The temperature at this time is 150° C., and the time is 10 minutes.

Comparative Examples 90 to 100

The steps were taken in accordance with the examples 90 to 100 except that the TE-ASH was employed instead of the TE-DAZ in the examples 90 to 100.

[Properties]

In the examples 90 to 100 and the comparative examples 90 to 100, the adhesive strength and the coverage ratio were investigated.

A result thereof is shown in Table-11.

TABLE 11

| | | Adhesiveness | |
|---|---|---|---|
| High polymerized materials (base A) Modified resin | Various types of materials (base B) | Adhesive strength (kN/m) | Coverage ratio (%) |
| Example 90 (Comparative example 90) | Sheet of modified crosslinked PE | PP | 3.1 (0) | 100 (0) |
| Example 91 (Comparative example 91) | Sheet of modified crosslinked PE | EP | 3.2 (0) | 100 (0) |
| Example 92 (Comparative example 92) | Sheet of modified crosslinked PE | PSt | 3.3 (0) | 100 (0) |
| Example 93 (Comparative example 93) | Sheet of modified crosslinked PE | PET | 1.1 (0) | 100 (0) |
| Example 94 (Comparative example 94) | Sheet of modified crosslinked PE | PC | 2.9 (0) | 100 (0) |
| Example 95 (Comparative example 95) | Sheet of modified crosslinked PE | POM | 3.1 (0) | 100 (0) |
| Example 96 (Comparative example 96) | Sheet of modified crosslinked PE | PBT | 3.2 (0) | 100 (0) |
| Example 97 (Comparative example 97) | Sheet of modified crosslinked PE | PPE | 3.2 (0) | 100 (0) |
| Example 98 (Comparative example 98) | Sheet of modified crosslinked PE | PI | 2.7 (0) | 100 (0) |
| Example 99 (Comparative example 99) | Sheet of modified crosslinked PE | PPS | 2.6 (0) | 100 (0) |
| Example 100 (Comparative example 100) | Sheet of modified crosslinked PE | LCP | 0.8 (0) | 100 (0) |

Examples 101 to 111

A sheet of vulcanized NBR rubber was employed as the base A.

An ethanol solution of 0.05 wt % TE-DAZ was blown away onto this sheet of vulcanized NBR rubber. Thereafter, the ultraviolet ray irradiation (30 mJ/cm$^2$) was performed.

The PP plate, the EP plate, the PSt plate, the PET plate, the PC plate, the POM plate, the PBT plate, the PPE plate, the PI plate, the PPS plate, and the LCP plate were prepared as the base B. The base B was also subjected to the treatment similar to that of a sheet of vulcanized NBR rubber.

The aforementioned base A and base B were arranged in such a manner that the surfaces of the modification treatment by the TE-DAZ faced each other. And, the press force of 2 MPa was applied. The temperature at this time is 120° C., and the time is 10 minutes.

Comparative Examples 101 to 111

The steps were taken in accordance with the examples 101 to 111 except that the TE-ASH was employed instead of the TE-DAZ in the examples 101 to 111.

[Properties]

In the examples 101 to 111 and the comparative examples 101 to 111, the adhesive strength and the coverage ratio were investigated.

A result thereof is shown in Table-12.

TABLE 12

| | Various materials to | Adhesiveness | |
|---|---|---|---|
| High polymerized material (base A) Modified resin | be subjected to surface treatment | Adhesive strength (kN/m) | Coverage ratio (%) |
| Example 101 (Comparative example 101) | Modified vulcanized NBR rubber | PP | 4.3 (0) | 100 (0) |
| Example 102 (Comparative example 102) | Modified vulcanized NBR rubber | EP | 4.2 (0) | 100 (0) |
| Example 103 (Comparative example 103) | Modified vulcanized NBR rubber | PSt | 4.8 (0) | 100 (0) |
| Example 104 (Comparative example 104) | Modified vulcanized NBR rubber | PET | 2.2 (0) | 100 (0) |
| Example 105 (Comparative example 105) | Modified vulcanized NBR rubber | PC | 4.6 (0) | 100 (0) |
| Example 106 (Comparative example 106) | Modified vulcanized NBR rubber | POM | 4.2 (0) | 100 (0) |
| Example 107 (Comparative example 107) | Modified vulcanized NBR rubber | PBT | 4.6 (0) | 100 (0) |
| Example 108 (Comparative example 108) | Modified vulcanized NBR rubber | PPE | 4.4 (0) | 100 (0) |
| Example 109 (Comparative example 109) | Modified vulcanized NBR rubber | PI | 4.3 (0) | 100 (0) |
| Example 110 (Comparative example 110) | Modified vulcanized NBR rubber | PPS | 2.9 (0) | 100 (0) |
| Example 111 (Comparative example 111) | Modified vulcanized NBR rubber | LCP | 1.9 (0) | 100 (0) |

Examples 112 to 122

A sheet of PP was employed as the base A.

An ethanol solution of the TE-DAZ was blown away onto this sheet of PP. Thereafter, the ultraviolet ray irradiation (30 mJ/cm$^2$) was performed.

An Al plate, a SUS plate, a Ni plate, an Au plate, an Ag plate, a Cu plate, a Sn plate, an Al$_2$O$_3$ plate, a SiC plate, an AlN plate, and a C(C-073478 made by Nikola Co.) plate were prepared as the base B. Additionally, the Al plate, the SUS plate, the Ni plate, the Al$_2$O$_3$ plate, the SiC plate, and the AlN plate was immersed into an ethanol solution of 0.1 wt % vinylmethoxy siloxane polymer (VMM010 made by Gelest INC.) for five minutes. Thereafter, the heat treatment was performed at a temperature of 80° C. for ten minutes. Finally, the corona discharge treatment was performed. The Au plate, the Ag plate, and the Cu plate were immersed into an ethanol solution of 0.1 wt % TES for ten minutes. Thereafter, the heat treatment was performed at a temperature of 80° C. for ten minutes.

The aforementioned base A and base B were arranged in such a manner that the surfaces of the modification treatment by the TE-DAZ faced each other. And, the press force of 1 MPa was applied. The temperature at this time is 160° C., and the time is 10 minutes.

Comparative Examples 112 to 122

The steps were taken in accordance with the examples 112 to 122 except that the TE-ASH was employed instead of the TE-DAZ in the examples 112 to 122.

[Properties]

In the examples 112 to 122 and the comparative examples 112 to 122, the adhesive strength and the coverage ratio were investigated.

A result thereof is shown in Table-13.

TABLE 13

| | | Various types of materials (base B) | Adhesiveness | |
|---|---|---|---|---|
| | High polymerized material (base A) Modified resin | | Adhesive strength (kN/m) | Coverage ratio (%) |
| Example 112 (Comparative example 112) | Sheet of modified PP | Al | 4.9 (0) | 100 (0) |
| Example 113 (Comparative example 113) | Sheet of modified PP | SUS | 4.2 (0) | 100 (0) |
| Example 114 (Comparative example 114) | Sheet of modified PP | Ni | 4.3 (0) | 100 (0) |
| Example 115 (Comparative example 115) | Sheet of modified PP | Au | 4.9 (0) | 100 (0) |
| Example 116 (Comparative example 116) | Sheet of modified PP | Ag | 4.1 (0) | 100 (0) |
| Example 117 (Comparative example 117) | Sheet of modified PP | Cu | 5.2 (0) | 100 (0) |
| Example 118 (Comparative example 118) | Sheet of modified PP | Sn | 4.6 (0) | 100 (0) |
| Example 119 (Comparative example 119) | Sheet of modified PP | $Al_2O_3$ | 4.3 (0) | 100 (0) |
| Example 120 (Comparative example 120) | Sheet of modified PP | SiC | 4.4 (0) | 100 (0) |
| Example 121 (Comparative example 121) | Sheet of modified PP | AlN | 3.8 (0) | 100 (0) |
| Example 122 (Comparative example 122) | Sheet of modified PP | C | 3.1 (0) | 100 (0) |

Examples 123 to 133

A sheet of crosslinked FKM was employed as the base A.
An ethanol solution of the TE-DAZ was blown away onto this sheet of crosslinked FKM. Thereafter, the ultraviolet ray irradiation (30 mJ/cm$^2$) was performed.

The Al plate, the SUS plate, the Ni plate, the Au plate, the Ag plate, the Cu plate, the Sn plate, the $Al_2O_3$ plate, the SiC plate, the AlN plate, and the C(C-073478 made by Nikola Co.) plate were prepared as the base B. Additionally, the Al plate, the SUS plate, the Ni plate, the $Al_2O_3$ plate, the SiC plate, and the MN plate was immersed into an ethanol solution of 0.1 wt % vinylmethoxy siloxane polymer (VMM010 made by Gelest INC.) for five minutes. Thereafter, the heat treatment was performed at a temperature of 80° C. for ten minutes. Finally, the corona discharge treatment was performed. The Au plate, the Ag plate, and the Cu plate was immersed into an ethanol solution of 0.1 wt % TES for ten minutes. Thereafter, the heat treatment was performed at a temperature of 80° C. for ten minutes.

The aforementioned base A and base B were arranged in such a manner that the surfaces of the modification treatment by the TE-DAZ faced each other. And, the press force of 1 MPa was applied. The temperature at this time is 160° C., and the time is 10 minutes.

Comparative Examples 123 to 133

The steps were taken in accordance with the examples 123 to 133 except that the TE-ASH was employed instead of the TE-DAZ in the examples 123 to 133.

[Properties]

In the examples 123 to 133 and the comparative examples 123 to 133, the adhesive strength and the coverage ratio were investigated.

A result thereof is shown in Table-14.

TABLE 14

| | | Various types of materials (base B) | Adhesiveness | |
|---|---|---|---|---|
| | High polymerized material (base A) Modified resin | | Adhesive strength (kN/m) | Coverage ratio (%) |
| Example 123 (Comparative example 123) | Sheet of modified crosslinked FKM | Al | 5.1 (0) | 100 (0) |
| Example 124 (Comparative example 124) | Sheet of modified crosslinked FKM | SUS | 4.8 (0) | 100 (0) |
| Example 125 (Comparative example 125) | Sheet of modified crosslinked FKM | Ni | 4.2 (0) | 100 (0) |
| Example 126 (Comparative example 126) | Sheet of modified crosslinked FKM | Au | 4.1 (0) | 100 (0) |
| Example 127 (Comparative example 127) | Sheet of modified crosslinked FKM | Ag | 3.9 (0) | 100 (0) |
| Example 128 (Comparative example 128) | Sheet of modified crosslinked FKM | Cu | 5.2 (0) | 100 (0) |
| Example 129 (Comparative example 129) | Sheet of modified crosslinked FKM | Sn | 3.8 (0) | 100 (0) |
| Example 130 (Comparative example 130) | Sheet of modified crosslinked FKM | $Al_2O_3$ | 4.1 (0) | 100 (0) |
| Example 131 (Comparative example 131) | Sheet of modified crosslinked FKM | SiC | 4.3 (0) | 100 (0) |
| Example 132 (Comparative example 132) | Sheet of modified crosslinked FKM | AlN | 4.5 (0) | 100 (0) |
| Example 133 (Comparative example 133) | Sheet of modified crosslinked FKM | C | 3.1 (0) | 100 (0) |

Conventionally, the crosslinked FKM rubber and the metal (and ceramics) hardly adhered to each other even though the adhesive is used. However, when the compound (α) of the present invention is employed, it can be seen that the solid adhesion is obtained The above-mentioned example is a case in which the TE-DAZ was employed. Also in the case in which the BTE-DAZ and the TE-MAZ were employed instead of this TE-DAZ, it was confirmed that a result similar to that of the above-mention examples 61 to 133 was yielded.

(1) The Novel Compound α (—OH Imparting Agent)

Example A-4

0.1 mol (18.4 g) of cyanuric chloride was added to 200 ml of a THF solution at a temperature of −10° C. And, it was placed under a nitrogen environment. 100 ml of the THF solution containing 0.105 mol (35.0 g) of 11-aminoundecyl triethoxysilane and 0.105 mol (14.6 ml) of triethylamine was dripped in to this cyanuric chloride solution. The stirring continued to be performed for 30 minutes also after the dripping was finished. After the reaction was finished, the generated triethylamine hydrochloride was removed. THF was evaporated under depressurization (20 mm Hg) and the crude product was obtained. The obtained crude product was refined by the silica gel column chromatography. The obtained refined product was oil-formed. The amount thereof was 43.05 g (a yield: 89.4%).

The obtained refined product (compound) was identified by the element analysis measurement device, the NMR measurement device and the MS measurement device. As a result, the refined product was determined to be 6-(11-trietoxysilylundecylpropyl)amino-1,3,5-triazine-2,4-dichloride (TEU-DC).

TEU-DC
$^1$H NMR (400 MHz, CDCl$_3$) d 0.63 (t, J=8.0 Hz, 2H, CH2CH2Si), 1.23 (t, J=7.0 Hz, 9H, SiOCH2CH3), 1.24-1.42 (m, J=8.0 Hz, 16H, NHCH2CH2 (CH2)8CH2), 1.58 (quint, J=8.0 Hz, 2H, NHCHCH2CH2), 3.46 (q, J=8.0 Hz, 2H, NHCH2CH2), 3.81 (q, J=7.0 Hz, 6H, SiOCH2CH3), 5.82 (brs, 1H, NH)
$^{13}$C NMR (101 MHz, CDCl$_3$) d. 10.11, 18.27, 22.60, 26.40, 29.16, 29.28, 29.52, 29.57, 33.12, 41.34, 58.25, 166.88, 169.55, 170.47
EI-MS (70 eV) m/z 480 (M+)
Element analysis (actual value/calculated value) C: 49.7/49.89, H: 7.9/7.95, N: 11.7/11.64

24.1 g (0.050 mol) of the aforementioned TEU-DC was added to 200 ml of ethanol at a temperature of 50 to 60° C. And, it was placed under a nitrogen environment. 50 ml of ethanol containing 0.102 mol of NaN$_3$ was dripped into this TEU-DC solution while it was stirred. The stirring continued to be performed for seven hours also after the dripping was finished. The deposited salts were filtered. Thereafter, ethanol was removed with the rotary evaporator. Next, isopropyl alcohol (IPA) and water were employed for re-precipitation. The deposited crystal was filtered. Thereafter, the drying was performed. The obtained refined product was oil-formed. The amount thereof was 23.5 g (a yield: 95.2%).

The obtained refined product (compound) was identified by the element analysis measurement device, the NMR measurement device and the MS measurement device. As a result, the refined product was determined to be 6-(11-trietoxysilylundecyl)amino-1,3,5-triazine-2,4-diazide (TEU-DAZ).

TEU-DAZ
$^1$H NMR (400 MHz, CDCl$_3$) d 0.63 (t, J=8.0 Hz, 2H, CH2CH2Si), 1.23 (t, J=7.0 Hz, 9H, SiOCH2CH3), 1.24-1.42 (m, J=8.0 Hz, 16H, NHCH2CH2 (CH2) 8CH2), 1.58 (quint, J=8.0 Hz, 2H, NHCHCH2CH2), 3.46 (q, J=8.0 Hz, 2H, NHCH2CH2), 3.81 (q, J=7.0 Hz, 6H, SiOCH2CH3), 5.98 (br s, 1H, NH)
$^{13}$C NMR (101 MHz, CDCl$_3$) d. 10.38, 18.29, 22.74, 26.37, 29.22, 29.26, 29.49, 29.55, 33.17, 41.15, 58.27, 166.91, 169.63, 170.43
EI-MS (70 eV) m/z 494 (M+)
Element analysis (actual value/calculated value) C: 48.4/48.56, H: 7.8/7.74, N: 28.1/28.32

Example A-5

5.0 g (0.027 mol) of cyanuric chloride was added to 50 ml of a THF solution at a temperature of −10° C. And, it was placed under a nitrogen environment. 30 ml of the THF solution containing 5.2 g (0.027 mol) of 3-aminopropyl diethoxymethylsilane and 3.8 g (0.038 mol) of triethylamine was dripped into this cyanuric chloride solution. The stirring continued to be performed for two hours also after the dripping was finished. After the reaction was finished, the generated triethylamine hydrochloride was removed. THF was evaporated under depressurization (20 mm Hg), and the product was obtained. The obtained product was oil-formed. The amount thereof was 9.19 g (a yield: 100.0%). The obtained product (compound) was identified by the element analysis measurement device, the NMR measurement device and the MS measurement device. As a result, the refined product was determined to be 6-(3-dietoxymethylsilylpropyl)amino-1,3,5-triazine-2,4-dichloride (DEM-DC).

DEM-DC
$^1$H NMR (400 MHz, CDCl$_3$) d 0.14 (s, J=8.0 Hz, 3H, CH2CH2SiCH3), 0.65 (t, J=8.0 Hz, 2H, CH2CH2Si), 1.23 (t, J=7.0 Hz, 6H, SiOCH2CH3), 1.71 (quint, J=8.0 Hz, 2H, NHCHCH2CH2), 3.50 (q, J=8.0 Hz, 2H, NHCH2CH2), 3.77 (q, J=7.0 Hz, 4H, SiOCH2CH3), 6.72 (br s, 1H, NH)
$^{13}$C NMR (101 MHz, CDCl$_3$) d. −4.99, 11.18, 18.33, 22.35, 43.85, 58.32, 165.79, 169.65, 170.85
EI-MS (70 eV) m/z 450 (M+)
Element analysis (actual value/calculated value) C: 38.8/38.94, H: 6.0/5.94, N: 16.5/16.51

9.19 g (0.027 mol) of the aforementioned DEM-DC was added to 100 ml of methanol at a temperature of 50 to 60° C. And, it was placed under a nitrogen environment. 50 ml of methanol containing 3.8 g (0.059 mol) of NaN$_3$ was dripped into this DEM-DC solution while it was stirred. The stirring continued to be performed for three hours also after the dripping was finished. Methanol was evaporated under depressurization (20 mm Hg) and the crude product was obtained. 200 ml of ether was added to this crude product. The generated salts and an excess amount of NaN$_3$ were removed. It was refined by the silica gel column chromatography. The obtained refined product was white powder. The amount thereof was 9.2 g (a yield: 93%).

The obtained refined product (compound) was identified by the element analysis measurement device, the NMR measurement device and the MS measurement device. As a result, the refined product was determined to be 6-(3-dietoxymethylsilylpropyl)amino-1,3,5-triazine-2,4-diazide (DEM-DAZ).

DEM-DAZ
$^1$H NMR (400 MHz, CDCl$_3$) d 0.13 (s, J=8.0 Hz, 3H, CH2CH2SiCH3), 0.65 (t, J=8.0 Hz, 2H, CH2CH2Si), 1.22 (t, J=7.0 Hz, 6H, SiOCH2CH3), 1.69 (quint, J=8.0 Hz, 2H, NHCHCH2CH2), 3.45 (q, J=8.0 Hz, 2H, NHCH2CH2), 3.77 (q, J=7.0 Hz, 4H, SiOCH2CH3), 6.29 (br s, 1H, NH)
$^{13}$C NMR (101 MHz, CDCl$_3$) d. −4.99, 11.24, 18.36, 22.65, 43.61, 58.26, 166.89, 169.66, 170.85
EI-MS (70 eV) m/z 352 (M+)
Element analysis (actual value/calculated value) C: 37.3/37.49, H: 5.6/5.72, N: 39.8/39.74

Example A-6

10.0 g (0.054 mol) of cyanuric chloride was added to 100 ml of a THF solution at a temperature of −10° C. And, it was placed under a nitrogen environment. 60 ml of the THF solution containing 12.8 g (0.054 mol) of 4-aminobutyltriethoxysilane and 7.7 g (0.075 mol) of triethylamine was dripped into this cyanuric chloride solution. The stirring continued to be performed for two hours also after the dripping was finished. After the reaction was finished, the generated triethylamine hydrochloride was removed. THF was evaporated under depressurization (20 mm Hg), and the crude product was obtained. The obtained crude product was refined by the silica gel column chromatography. The obtained refined product was oil-formed. The amount thereof was 17.1 g (a yield: 83.0%).

The refined obtained product (compound) was identified by the element analysis measurement device, the NMR measurement device and the MS measurement device. As a result, the refined product was determined to be 6-(4-trietoxysilyl-butyl)amino-1,3,5-triazine-2,4-dichloride (TEB-DC).

TEB-DC $^1$H NMR (400 MHz, CDCl$_3$) d 0.65 (t, J=8.0 Hz, 2H, CH2CH2Si), 1.22 (t, J=7.0 Hz, 9H, SiOCH2CH3), 1.50 (quint, J=8.0 Hz, 2H, CH2CH2Si), 1.71 (quint, J=8.0 Hz, 2H, NHCH2CH2CH2), 3.50 (q, J=8.0 Hz, 2H, NHCH2CH2), 3.82 (q, J=7.0 Hz, 6H, SiOCH2CH3), 6.70 (br s, 1H, NH)

$^{13}$C NMR (101 MHz, CDCl$_3$) d. 9.98, 18.25, 20.06, 31.92, 41.16, 58.34, 165.76, 169.56, 170.90

EI-MS (70 eV) m/z 383 (M+)

Element analysis (actual value/calculated value) C: 40.6/40.73, H: 6.3/6.31, N: 14.6/16.62

15.0 g (0.039 mol) of the aforementioned TEB-DC was added to 100 ml of methanol at a temperature of 50 to 60° C. And, it was placed under a nitrogen environment. 50 ml of methanol containing 5.6 g (0.086 mol) of NaN$_3$ was dripped in this TEB-DC solution while it was stirred. The stirring continued to be performed for three hours also after the dripping was finished. Methanol was evaporated under depressurization (20 mm Hg) and the crude product was obtained. 200 ml of ether was added to this crude product. The generated salts and an excess amount of NaN$_3$ were removed. It was refined by the silica gel column chromatography. The obtained refined product was white powder. The amount thereof was 14.0 g (a yield: 97.2%). The obtained refined product (compound) was identified by the element analysis measurement device, the NMR measurement device and the MS measurement device. As a result, the refined product was determined to be 6-(4-trietoxysilylbutyl)amino-1,3,5-triazine-2,4-diazide (TEB-DAZ).

TEB-DAZ $^1$H NMR (400 MHz, CDCl$_3$) d 0.66 (t, J=8.0 Hz, 2H, CH2CH2Si), 1.22 (t, J=7.0 Hz, 9H, SiOCH2CH3), 1.50 (quint, J=8.0 Hz, 2H, CH2CH2Si), 1.65 (quint, J=8.0 Hz, 2H, NHCH2CH2CH2), 3.45 (q, J=8.0 Hz, 2H, NHCH2CH2), 3.81 (q, J=7.0 Hz, 6H, SiOCH2CH3), 6.06 (br s, 1H, NH)

$^{13}$C NMR (101 MHz, CDCl$_3$) d. 10.03, 18.27, 20.10, 31.23, 40.74, 58.39, 65.90, 169.63, 170.43

EI-MS (70 eV) m/z 396 (M+)

Element analysis (actual value/calculated value) C: 39.4/39.38, H: 6.0/6.10, N: 35.2/35.33

Example A-7

7.43 g (0.040 mol) of cyanuric chloride was put in a three-mouth eggplant flask (200 mL). In addition, 80 mL of acetone was added. Thereafter, it was cooled to a temperature of 0° C. After cooling, 40 mL of an aqueous solution containing 4.06 g (0.039 mol) of diethanolamine was dripped. Next, 30 mL of an aqueous solution containing 1 mol of NaOH was dripped. The stirring was performed for 90 minutes at a temperature of 0° C. after the dripping. After standing, a precipitated white solid was filtered with suction filtering. After the filtering, decompression drying was performed. As a result, a colorless solid was obtained. The yield amount was 8.1 g (a separation yield: 81%).

The product was identified by an element analysis measurement device, an NMR measurement device and an MS measurement device. As a result, the product was determined to be 6-(N,N-dihydroxyethyl)amino-1,3,5-triazine-2,4-dichloride (DEA-DC).

DEA-DC $^1$H NMR (101 MHz, DMSO-d6) d 3.58 (t, J=5.6 Hz, 4H, N(CH2CH2OH)2), 3.66 (t, J=5.6 Hz, 4H, N(CH2CH2OH)$_2$), 4.96 (br s, 2H, N(CH2CH2OH)2); $^{13}$C NMR (101 MHz, DMSO-d6) d 50.8, 57.7, 164.3, 168.7

EI-MS (70 eV) m/z 252 (M+).

Element analysis (actual value/calculated value) C: 33.0/33.22, H: 4.1/3.90

5.06 g (0.020 mol) of the DEA-DC was put in the three-mouth eggplant flask (500 mL). The inside of the flask was put under an argon environment. Thereafter, 100 mL of the DMF was added. Next, 2.67 g (0.041 mmol) of NaN$_3$ was added. Thereafter, the stirring at a room temperature was performed for two hours, and next, the stirring at a temperature of 50° C. was performed for one hour. After the cooling to a room temperature was performed, 100 mL of water and 100 mL of dietyl ether were added. And, it stood at a room temperature. A while solid precipitated by this was filtered with the suction filtering. Thereafter, the decompression drying was performed. As a result, colorless powder was obtained. The yield amount was 4.53 g (a separation yield: 85%).

The product was identified by the element analysis measurement device, the NMR measurement device and the MS measurement device. As a result, the product was determined to be 6-(N,N-dihydroxyethyl)amino-1,3,5-triazine-2,4-diazide (DEA-DAZ).

DEA-DAZ $^1$H NMR (101 MHz, DMSO-d6) δ 3.58 (t, J=5.4 Hz, 4H, N(CH2CH2OH)2), 3.65 (t, J=5.4 Hz, 4H, N(CH2CH2OH)2), 4.79 (t, J=5.4 Hz, 2H, N(CH2CH2OH)2); $^{13}$C NMR (101 MHz, DMSO-d6) δ 50.6, 58.1, 165.3, 169.1

EI-MS (70 eV) m/z 266 (M+).

Element analysis (actual value/calculated value) C: 31.3/31.58, H: 3.9/3.79, N: 52.4/52.61

(2) Surface Modification by a Novel Compound α (—OH Imparting Agent)

Examples 134 to 136

The PP (polypropylene) plate subjected to the ultrasonic cleaning (time: 10 minutes) in ethanol of which a temperature is 40° C. was employed as the base A.

This PP plate was immersed (time: 5 minutes) into an ethanol solution (temperature: 20° C.) of the aforementioned TEU-DAZ, DEM-DAZ, and TEB-DAZ (concentration: 0.1 wt %). After lifting up, the warm-air drying was performed. Next, a high-pressure mercury lamp (output: 2 kW, EYEMI-NIGRANTAGE made by EYE GRAPHICS CO. Ltd.) was employed, and the ultraviolet ray irradiation of 30 mJ/cm$^2$ was performed. Thereafter, the ultrasonic cleaning was performed in the ethanol.

[Properties]

A result (presence or not of the triazine ring on the substrate surface, and presence or not of the alkoxysilyl group on the substrate surface: an XPS analysis (X-ray Photoelectron Spectroscopy: PHI-QunteraSXM made of ULVAC-PHI)) of the modification treatment by the aforementioned examples 134 to 136 is shown in Table-15.

TABLE 15

| | Compound (α) | XPS analysis (at %) | |
| --- | --- | --- | --- |
| | | N1s | Si2p |
| Example 134 | TEU-DAZ | 10.2 | 2.1 |
| Example 135 | DEM-DAZ | 16.1 | 3.3 |
| Example 136 | TEB-DAZ | 13.9 | 2.8 |

N1s indicates presence or not of the triazine ring, and Si2p indicates presence or not of the alkoxysilyl group in the Table-15. The fact that the numerical values of N1s and Si2p are confirmed indicates presence of alkoxysilylpropylamino triazinyliden group on the surface of the PP plate.

And, it can be seen from the aforementioned Table-15 and the aforementioned Table-1 that the aforementioned TEU-DAZ, DEM-DAZ, and TEB-DAZ also exhibit reactivity similar to that of the aforementioned TE-DAZ.

(3) Bonding (Adhesion: Molecular Adhesion) by a Novel Compound α (—OH Imparting Agent)

Examples 137 to 145

A sheet of PP was employed as the base A.

An ethanol solution of the aforementioned TEU-DAZ, DEM-DAZ, and TEB-DAZ (concentration: 0.1 wt %) was blown away onto this sheet of PP respectively. Thereafter, the ultraviolet ray irradiation (30 mJ/cm$^2$) was performed.

The Al plate, the Al$_2$O$_3$ plate, and the Q plate were prepared as the base B. Corona Master PS-1M (14 kV, 15 kHz, AC 100 V) made by Shinko Electric & Instrumentation Co., Ltd. was employed to perform the treatment at a temperature of 20° C. and for ten seconds. With this, the surface was made clean. And yet, —OH groups were generated on the surface.

The aforementioned base A and base B were arranged in such a manner that the surfaces of the modification treatment by the TEU-DAZ, the DEM-DAZ and the TEB-DAZ faced each other. And, the press force of 1 MPa was applied under vacuum. The temperature at this time is 160° C., and the time is 10 minutes.

Comparative Examples 137, 138, and 139

The steps were taken in accordance with the examples 137, 138, and 139 except that the TE-ASH was employed instead of the TEU-DAZ in the examples 137, 138, and 139.

[Properties]

In the examples 137 to 145 and the comparative examples 137, 138, and 139, the adhesive strength and the coverage ratio were investigated.

A result thereof is shown in Table-16.

TABLE 16

| | | | Adhesiveness | |
| --- | --- | --- | --- | --- |
| | Compound (α) | Base B | Adhesive strength (kN/m) | Coverage ratio (%) |
| Example 137 | TEU-DAZ | Al | 4.6 | 100 |
| Example 138 | TEU-DAZ | Al$_2$O$_3$ | 4.2 | 100 |
| Example 139 | TEU-DAZ | Q | 2.8 | 100 |
| Example 140 | DEM-DAZ | Al | 4.8 | 100 |
| Example 141 | DEM-DAZ | Al$_2$O$_3$ | 4.5 | 100 |
| Example 142 | DEM-DAZ | Q | 3.0 | 100 |
| Example 143 | TEB-DAZ | Al | 4.3 | 100 |
| Example 144 | TEB-DAZ | Al$_2$O$_3$ | 4.1 | 100 |
| Example 145 | TEB-DAZ | Q | 2.7 | 100 |

TABLE 16-continued

| | | | Adhesiveness | |
| --- | --- | --- | --- | --- |
| | Compound (α) | Base B | Adhesive strength (kN/m) | Coverage ratio (%) |
| Comparative example 137 | TE-ASH | Al | 0 | 0 |
| Comparative example 138 | TE-ASH | Al$_2$O$_3$ | 0 | 0 |
| Comparative example 139 | TE-ASH | Q | 0 | 0 |

It can be seen that the TEU-DAZ, DEM-DAZ, and TEB-DAZ also exhibit excellent adhesiveness similarly to the TE-DAZ etc.

This application is based upon and claims the benefit of priority from Japanese patent application No. 2010-220512, filed on Sep. 30, 2010, the disclosure of which is incorporated herein in its entirety by reference.

The invention claimed is:

1. A method of bonding a base A and a base B, the method comprising:
   (i) applying an agent comprising a compound α onto a surface of the base A;
   (ii) arranging the base B so that the base B faces the compound α on the base A; and
   (iii) applying force onto the base A, the base B, or both the base A and the base B to integrally bond the base A and the base B;
   wherein the compound α is a compound comprising an OH group or an OH yielding group, an azide group, and a triazine ring per molecule; and
   the base A is configured by employing a polymer.

2. The method according to claim 1, wherein in said applying (iii), the force is applied such that the OH group of the compound α on the base A or OH groups generated from the OH yielding group of the compound α on the base A contact a surface of the base B.

3. The method according to claim 1, wherein said applying (iii) occurs at a temperature of from 0 to 300° C.

4. The method according to claim 1, further comprising:
   (iv) irradiating the compound on the surface of the base A with a light having a predetermined pattern.

5. The method according to claim 4, wherein in said irradiating (iv), the base A and the azide group of the compound α react to each other, and the compound α is bonded to the surface of the base A.

6. The method according to claim 4, wherein the light is an ultraviolet ray.

7. The method according to claim 1, wherein the OH group or the OH yielding group is an alkoxysilyl group.

8. The method according to claim 1, wherein the compound α is a compound of a general formula [I],

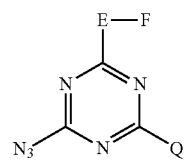

General formula [I]

wherein:

E is an arbitrary group;

F is the OH group or the OH yielding group; and

-Q is —N$_3$ or —NR$_1$(R$_2$), wherein each R$_1$ and R$_2$ is independently H, a hydrocarbon group comprising from 1 to 24 carbons, or a —RSi(R')$_n$(OA)$_{3-n}$, wherein R is a chain hydrocarbon group comprising from 1 to 12 carbons, R' is a chain hydrocarbon group comprising from 1 to 4 carbons, A is H or a chain hydrocarbon group comprising from 1 to 4 carbons, and n is an integer of from 0 to 2.

9. The method according to claim 1, wherein the compound α is a compound of a general formula [Io],

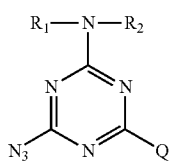

General formula [Io]

wherein:

-Q is —N$_3$ or —NR$_1$(R$_2$);

each R$_1$ and R$_2$ is independently H, a hydrocarbon group comprising from 1 to 24 carbons, or a —RSi(R')$_n$(OA)$_{3-n}$, wherein R is a chain hydrocarbon group comprising from 1 to 12 carbons, R' is a chain hydrocarbon group comprising from 1 to 4 carbons, A is H or a chain hydrocarbon group comprising from 1 to 4 carbons, and n is an integer of from 0 to 2; and at least one of R$_1$ and R$_2$ is —RSi(R')$_n$(OA)$_{3-n}$.

10. The method according to claim 1, wherein the compound α is a compound of a general formula [Ia],

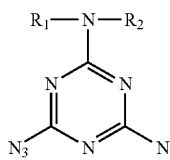

General formula [Ia]

wherein:

each R$_1$ and R$_2$ is independently H, a hydrocarbon group comprising from 1 to 24 carbons, or a —RSi(R')$_n$(OA)$_{3-n}$; wherein R is a chain hydrocarbon group comprising from 1 to 12 carbons, R' is a chain hydrocarbon group comprising from 1 to 4 carbons, A is H or a chain hydrocarbon group comprising from 1 to 4 carbons, and n is an integer of from 0 to 2; and at least one of R$_1$ and R$_2$ is —RSi(R')$_n$(OA)$_{3-n}$.

11. The bending method according to claim 1, wherein the compound α is a compound of a general formula [Ib],

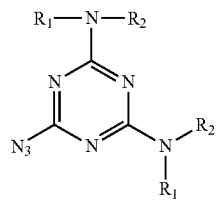

General formula [Ib]

wherein:

each R$_1$ and R$_2$ is independently H, a hydrocarbon group number of comprising from 1 to 24 carbons, or a —RSi(R')$_n$(OA)$_{3-n}$; wherein R is a chain hydrocarbon group comprising from 1 to 12 carbons, R' is a chain hydrocarbon group comprising from 1 to 4 carbons, A is H or a chain hydrocarbon group comprising from 1 to 4 carbons, and n is an integer of from 0 to 2; and at least one of all R$_1$s and all R$_2$s is —RSi(R')$_n$(OA)$_{3-n}$.

12. The method according to claim 1, further comprising:

(v) applying a substance of a general formula [II] onto a surface of the compound α after said applying (i) and before said arranging (ii),

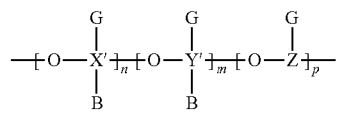

General formula [II]

wherein:

each of X' and Y' is independently Si or Ti;

Z is Al;

G is a hydrocarbon group comprising from 1 to 3 carbons or an alkoxy group comprising from 1 to 3 carbons;

B is an alkoxy group comprising from 1 to 3 carbons;

n and m each is an integer of from 0 to 200, (wherein 2≤n+m≤400; and p is an integer of from 0 to 100.

13. The method according to claim 12, further comprising:

(vi) applying a compound β comprising an alkoxysilyl group, an alkoxy alminate group, or an alkoxy titanate group onto the surface of the compound α after said applying (v) and before said arranging (ii).

14. The method according to claim 13, wherein the compound β is a compound of a general formula [T], L-Si(M')n(OM)3-*n*     General formula [T]

wherein:

L is an organic group, which optionally is aliphatic, aromatic, a chain, or cyclic and optionally comprises elements other than carbon and hydrogen;

each M' is independently a chain hydrocarbon group comprising from 1 to 4 carbons;

each M is H or a chain hydrocarbon group comprising from 1 to 4 carbons; and n is an integer of from 0 to 2.

15. The method according to claim 13, wherein the compound β is a compound of a general formula [III],

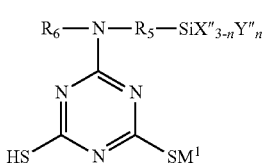

General formula [III]

wherein:

$R_5$ is a hydrocarbon group comprising 1 to 12 carbon;

$R_6$ is H or a hydrocarbon group comprising 1 to 10 carbon;

each X" is independently H or a hydrocarbon group comprising 1 to 10 carbon;

each Y" is independently an alkyloxy group comprising 1 to 10 carbon;

n is an integer of from 1 to 3; and

M¹ is H, Li, Na, K, or Cs.

16. The bonding method according to claim 13, wherein the compound β is a compound of a general formula [IV],

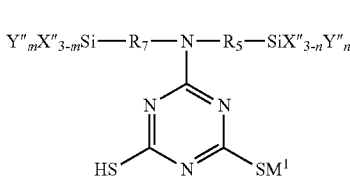

General formula [IV]

wherein:

$R_5$ is a hydrocarbon group comprising from 1 to 12 carbons;

$R_7$ is a hydrocarbon group comprising from 1 to 12 carbons;

each X" is independently H or a hydrocarbon group comprising from 1 to 10 carbons;

each Y" is independently an alkyloxy group comprising from 1 to 10 carbons;

n and m each is an integer of from 1 to 3; and

M¹ is H, Li, Na, K or Cs.

17. The method according to claim 1, further comprising:

(vi) applying a compound β comprising an alkoxysilyl group, an alkoxy alminate group, or an alkoxy titanate group onto a surface of the compound α after said applying (i) and before said arranging (ii).

18. The method according to claim 17, wherein the compound β is a compound of a general formula [T],

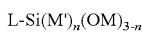

General formula [T]

wherein:

L is an organic group, which optionally is aliphatic, aromatic, a chain, or cyclic and optionally comprises elements other than carbon and hydrogen;

each M' is independently a chain hydrocarbon group comprising from 1 to 4 carbons;

each M is independently H or a chain hydrocarbon group comprising from 1 to 4 carbons; and n is an integer of from 0 to 2.

19. The method according to claim 17, wherein the compound β is a compound of a general formula [III],

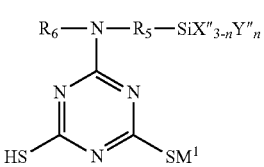

General formula [III]

wherein:

$R_5$ is a hydrocarbon group comprising from 1 to 12 carbons;

$R_6$ is H or a hydrocarbon group comprising from 1 to 10 carbons;

each X" is independently H or a hydrocarbon group comprising from 1 to 10 carbons;

each Y" is independently an alkyloxy group comprising from 1 to 10 carbons;

n is an integer of from 1 to 3; and

M¹ is H, Li, Na, K or Cs.

20. The method according to claim 17, wherein the compound β is a compound of a general formula [IV],

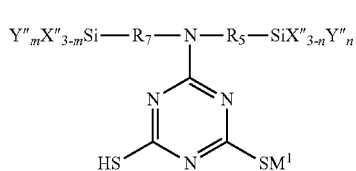

General formula [IV]

wherein:

$R_5$ is a hydrocarbon group comprising from 1 to 12 carbons;

$R_7$ is a hydrocarbon group comprising from 1 to 12 carbons;

each X" is independently H or a hydrocarbon group comprising from 1 to 10 carbons;

each Y" is independently an alkyloxy group comprising from 1 to 10 carbons;

n and m each is an integer of from 1 to 3; and

M¹ is H, Li, Na, K or Cs.

21. The method according to claim 1, wherein the compound α is at least one selected from the group consisting of 6-azide-2,4-bis(ethanolamino)-1,3,5-triazine, 6-azide-2,4-bis(hexanolamino)-1,3,5-triazine, 6-azide-2,4-bis(decanolamino)-1,3,5-triazine, 6-azide-2,4-bis(3,4-bishydroxyphenyl)amino)-1,3,5-triazine, 6-azide-2,4-bis(2,2-dihydroxymethyl)ethylamino-1,3,5-triazine, 6-azide-2,4-bis(tris methanol methyl)methylamino-1,3,5-triazine, 6-azide-2,4-(1,2-dihydroxypropyl)amino-1,3,5-triazine, 6-azide-2,4-bis(3-triethoxysilyl)propylamino-1,3,5-triazine (TE-MAZ), 6-azide-2,4-bis(3-methylethylketoxyminosilyl)propylamino-1,3,5-triazine, 6-azide-2,4-bis(3-methylethylketoxyminosilyl)propylamino-1,3,5-triazine, 6-azide-2,4-bis(3-triisopropoxysilyl)propylamino-1,3,5-triazine, 6-azide-2,4-bis(3-triacetoxysilyl)propylamino-1,3,5-triazine, 6-azide-2,4-bis(3-triisopropoxysilyl)propylamino-1,3,5-triazine, 6-azide-2,4-bis(3-triisopropoxysilyl)propylamino-1,3,5-triazine, 6-azide-2,4-bis(3-tribenzoxysilyl)propylamino-1,3,5-triazine, 6-azide-2,4-bis(diethanolamino)-1,3,5-triazine, 6-azide-2,4-bis(dihexanolamino)-1,3,5-triazine, 6-azide-2,4-bis(didecanolamino)-1,3,5-triazine, 6-azide-2,4-bis(3-triethoxysilylpropyl)amino-1,3,5-triazine, 6-azide-2,4-bis(6-triethoxysilylhexyl)amino-1,3,5-triazine, 6-azide-2,4-bis(10-triethoxysilyldodecyl)amino-1,3,5-triazine, 2,4-diazide- 6-(N,N-diethanol)amino-1,3,5-triazine (DEA-DAZ), 2,4-diazide-6-(N,N-didecanol)amino-1,3,5-triazine, 2,4-diazide-6-(3,4-bishydroxyphenyl)amino-1,3,5-triazine, 2,4-diazide-6-(2,2-dihydroxymethyl)ethylamino-1,3,5-triazine, 2,4-diazide-6-(tris methanol methyl)methylamino-1,3,5-triazine, 2,4-diazide-6-(1,2-dihydroxypropyl)amino-1,3,5-triazine, 2,4-diazide-6-(3-triethoxysilylpropyl)amino-1,3,5-triazine (TE-DAZ), 2,4-diazide-6-bis(3-methylethylketoxyminosilyl)propylamino-1,3,5-triazine, 2,4-diazide-6-bis(3-methylethylketoxyminosilyl)propylamino-1,3,5-triazine, triisopropoxysilyl)propylamino-1,3,5-triazine, 2,4-diazide-6-(3-triacetoxysilyl)propylamino-1,3,5-triazine, 2,4-diazide-6-(3-triisopropoxysilyl)propylamino-1,3,5-triazine, 2,4-diazide-6-(3-triisopropoxysilyl)propylamino-1,3,5-triazine, 2,4-diazide-6-(3-tribenzoxysilyl)propylamino-1,3,5-triazine, 2,4-diazide-6-bis(dihydroxyethyl)amino-1,3,5-triazine, 2,4-diazide-6-(N,N-dihexanol)amino-1,3,5-triazine, 2,4-diazide-6-(N,N-didecanol)amino-1,3,5-triazine, 2,4-diazide-6-(N,N-bis(3-triethoxysilylpropyl)amino-1,3,5-triazine (BTE-DAZ), 2,4-diazide-6-(N,N-bis(6-triethoxysilylhexyl)amino-1,3,5-triazine, 6-(11-triethoxysilylundecyl)amino-1,3,5-triazine-2,4-diazide (TEU-DAZ), 6-(3-diethoxymethylsilylpropyl)amino-1,3,5-triazine-2,4-diazide (DEM-DAZ), and 6-(4-triethoxysilylbutyl)amino-1,3,5-triazine-2,4-diazide (TEB-DAZ).

22. A bonded body produced by the method according to claim 1.

* * * * *